US010577585B2

(12) United States Patent
Nguyen et al.

(10) Patent No.: US 10,577,585 B2
(45) Date of Patent: Mar. 3, 2020

(54) CELL EXPANSION

(71) Applicant: Terumo BCT, Inc., Lakewood, CO (US)

(72) Inventors: Kim Thien Duy Nguyen, Durham, NC (US); Thomas Patrick Startz, Scarsdale, NY (US); Alexander L. Howard, Denver, CO (US)

(73) Assignee: Terumo BCT, Inc., Lakewood, CO (US)

( * ) Notice: Subject to any disclaimer, the term of this patent is extended or adjusted under 35 U.S.C. 154(b) by 431 days.

(21) Appl. No.: 15/153,396

(22) Filed: May 12, 2016

(65) Prior Publication Data

US 2016/0333314 A1 Nov. 17, 2016

Related U.S. Application Data

(60) Provisional application No. 62/161,128, filed on May 13, 2015.

(51) Int. Cl.
| | |
|---|---|
| *C12N 5/0783* | (2010.01) |
| *C12M 3/00* | (2006.01) |
| *C12M 1/12* | (2006.01) |
| *C12M 1/02* | (2006.01) |
| *C12M 1/36* | (2006.01) |

(52) U.S. Cl.
CPC .......... *C12N 5/0636* (2013.01); *C12M 21/08* (2013.01); *C12M 23/06* (2013.01); *C12M 23/44* (2013.01); *C12M 25/10* (2013.01); *C12M 27/00* (2013.01); *C12M 41/48* (2013.01); *C12N 5/0638* (2013.01); *C12N 2501/2302* (2013.01); *C12N 2501/2307* (2013.01); *C12N 2501/2312* (2013.01); *C12N 2501/2315* (2013.01); *C12N 2501/51* (2013.01); *C12N 2501/515* (2013.01); *C12N 2527/00* (2013.01)

(58) Field of Classification Search
CPC .... C12N 2501/2302; C12N 2501/2307; C12N 2501/2312; C12N 2501/2315; C12N 5/0636; C12N 55/0637; C12N 55/0638; C12N 5/0637; C12N 5/0638
See application file for complete search history.

(56) References Cited

U.S. PATENT DOCUMENTS

2014/0112956 A1* 4/2014 Karlsson-Parra ...... A61K 35/17
424/277.1
2016/0137980 A1* 5/2016 Abbot .................. C12N 5/0636
435/375

OTHER PUBLICATIONS

Lamers et al., Large-scale production of natural cytokines during activation and expansion of human T lymphocytes in hollow fiber bioreactor cultures. Journal of Immunotherapy, vol. 22 No. 4 (1999) pp. 299-307. (Year: 1999).*

* cited by examiner

*Primary Examiner* — Kara D Johnson
(74) *Attorney, Agent, or Firm* — Terumo BCT, Inc. IP Law Department

(57) ABSTRACT

Embodiments are described that relate to methods and systems for growing cells in a hollow fiber bioreactor. In embodiments, the cells may be exposed to an activator for activating expansion of the cells. The cells may in embodiments include T cells, and the activator may be in different forms, including, for example, antigen presenting cells or beads functionalized with antibodies.

10 Claims, 15 Drawing Sheets

CELL EXPANSION

CROSS-REFERENCE TO RELATED APPLICATION(S)

This patent application claims priority to U.S. Provisional Patent Application No. 62/161,128, entitled "CELL EXPANSION," filed May 13, 2015 and hereby incorporated by reference in its entirety as if set forth herein in full.

BACKGROUND

Cell Expansion Systems (CESs) may be used to expand and differentiate a variety of cell types that may be used for both research and therapeutic purposes. As one example, T cell therapies (e.g., autologous T cell therapies) are an emerging technology for treatment of numerous diseases. T cells that are genetically engineered and expanded ex vivo, e.g., may show promise for treatment of some leukemias (e.g., B cell) and other cancers. Currently, expansion of T cells may occur in bag systems or systems that are not fully automated and are also not functionally closed.

Embodiments have been made in light of these and other considerations. However, the relatively specific problems discussed above do not limit the applicability of the embodiments of the present disclosure.

SUMMARY

The summary is provided to introduce aspects of some embodiments in a simplified form, and is not intended to identify key or essential elements, nor is it intended to limit the scope of the claims.

Embodiments relate to cell expansion systems (CESs) and methods of growing cells in a bioreactor of a cell expansion system. Embodiments provide methods for expanding cells in a bioreactor, such as a hollow fiber bioreactor. Embodiments may provide for introducing cells (e.g., T cells) into a hollow fiber bioreactor, wherein the hollow fiber bioreactor includes a plurality of hollow fibers. Embodiments may provide for exposing the first plurality of cells to an activator to activate expansion of the cells in the hollow fiber bioreactor. In embodiments, the activator may be a cell, an immobilized antigen (e.g., on a bead), or a soluble antigen. After exposing the cells to the activator, the cells may be expanded to generate a second plurality of expanded cells. The second plurality of expanded cells may then be removed from the bioreactor.

Other embodiments provide for a cell expansion system for expanding cells. In embodiments, the system may include a hollow fiber bioreactor comprising a first fluid flow path having at least opposing ends, wherein a first opposing end of the first fluid flow path is fluidly associated with a first port of the hollow fiber bioreactor, and a second end of the first fluid flow path is fluidly associated with a second port of the hollow fiber bioreactor, wherein the first fluid flow path comprises an intracapillary portion of the hollow fiber bioreactor. A fluid inlet path fluidly associated with the first fluid flow path may be used to introduce a plurality of cells into the first fluid flow path. Embodiments may further include a pump for circulating fluid in the first fluid flow path.

System may include a processor for executing instructions so that when instructions are executed by the processor a method that includes introducing a first fluid comprising a first plurality of cells comprising leukocytes into the intracapillary portion of the hollow fiber bioreactor is performed. The processor may further execute instructions that provide for exposing the first plurality of cells to a first activator in the intracapillary portion to activate expansion of the cells in the hollow fiber bioreactor. The processor may execute instructions that provide for introducing a second fluid comprising media into the intracapillary portion to expand at least a portion of the first plurality of cells and generate a second plurality of expanded cells. The processor may execute instructions that provide for removing the second plurality of expanded cells from the bioreactor.

BRIEF DESCRIPTION OF THE DRAWINGS

Non-limiting and non-exhaustive embodiments are described with reference to the following figures.

DETAILED DESCRIPTION

Figure 1:
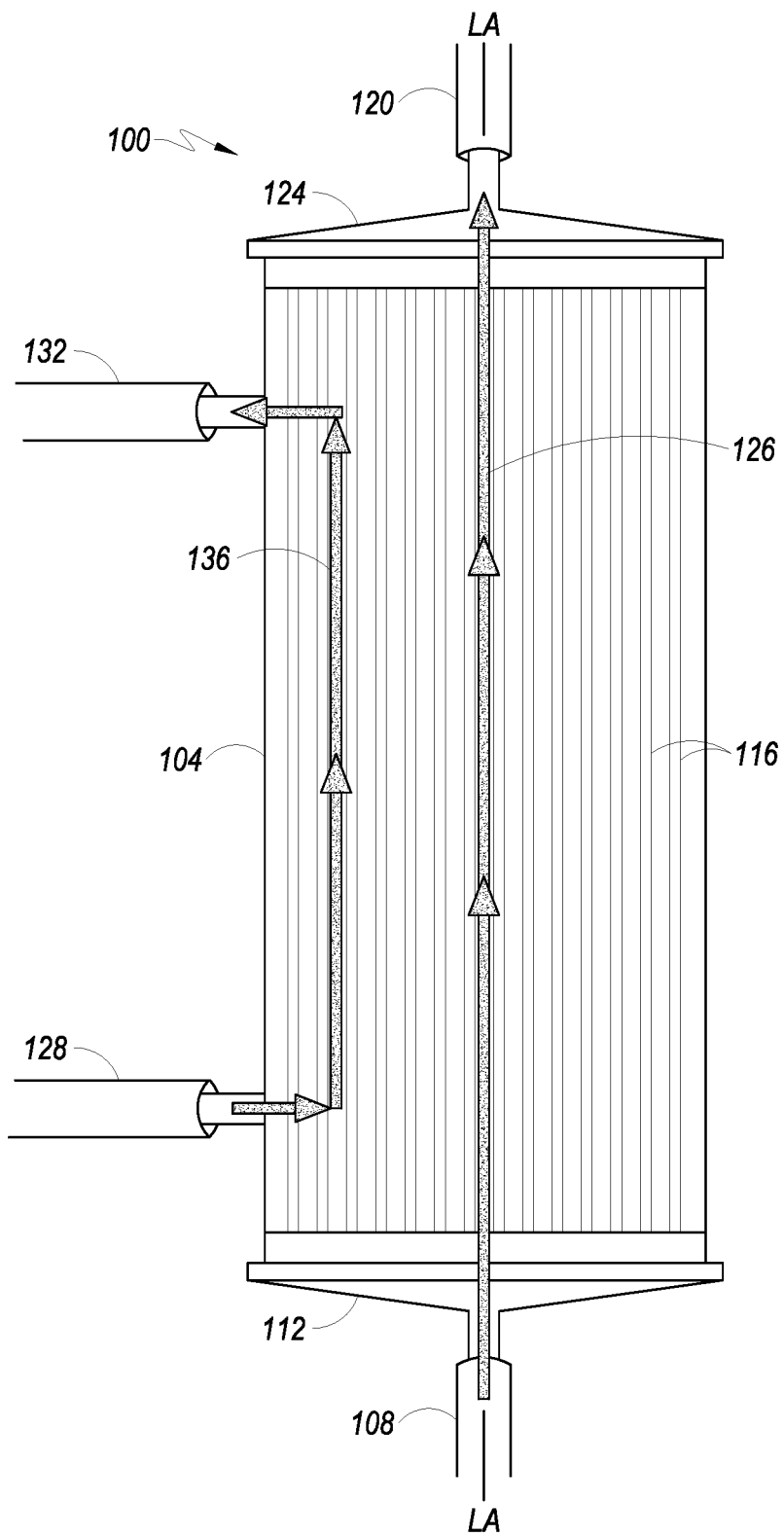
FIG. 1 depicts a perspective view of a hollow fiber bioreactor, in accordance with embodiments.

The principles of the present disclosure may be further understood by reference to the following detailed description and the embodiments depicted in the accompanying drawings. It should be understood that although specific features are shown and described below with respect to detailed embodiments, the present disclosure is not limited to the embodiments described below.

Reference will now be made in detail to the embodiments illustrated in the accompanying drawings and described below. Wherever possible, the same reference numerals are used in the drawings and the description to refer to the same or like parts.

Referring to FIG. 1, an example of a hollow fiber bioreactor 100, which may be used with the present disclosure is shown in front side elevation view. Hollow fiber bioreactor 100 has a longitudinal axis LA-LA and includes chamber housing 104. In at least one embodiment, chamber housing 104 includes four openings or ports: IC inlet port 108, IC outlet port 120, EC inlet port 128, and EC outlet port 132.

According to embodiments of the present disclosure, fluid in a first circulation path enters hollow fiber bioreactor 100 through IC inlet port 108 at a first longitudinal end 112 of the hollow fiber bioreactor 100, passes into and through the intracapillary side (referred to in various embodiments as the intracapillary ("IC") side or "IC space" of a hollow fiber membrane) of a plurality of hollow fibers 116, and out of hollow fiber bioreactor 100 through IC outlet port 120 located at a second longitudinal end 124 of the hollow fiber bioreactor 100. The fluid path between the IC inlet port 108 and the IC outlet port 120 defines the IC portion 126 of the hollow fiber bioreactor 100. Fluid in a second circulation path flows in the hollow fiber bioreactor 100 through EC inlet port 128, comes in contact with the extracapillary side or outside (referred to as the "EC side" or "EC space" of the membrane) of the hollow fibers 116, and exits hollow fiber bioreactor 100 via EC outlet port 132. The fluid path between the EC inlet port 128 and the EC outlet port 132 comprises the EC portion 136 of the hollow fiber bioreactor 100. Fluid entering hollow fiber bioreactor 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and remain in the IC space of the hollow fibers 116. The media may be replaced as needed, in embodiments. Media may also be circulated through an oxygenator or gas transfer module to exchange gasses as needed (see e.g., cell expansion systems 500 (FIG. 5) and 600 (FIG. 6)). Cells may be contained within a first circulation path and/or a second circulation path, as described below, and may be on either the IC side and/or EC side of the membrane, according to embodiments.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, or by exposing the surface to radiation. Gamma treating the membrane surface allows for attachment of adherent cells without additionally coating the membrane with fibronectin or the like. Bioreactors made of gamma treated membranes may be reused. Other coatings and/or treatments for cell attachment may be used in accordance with embodiments of the present disclosure.

Figure 2:
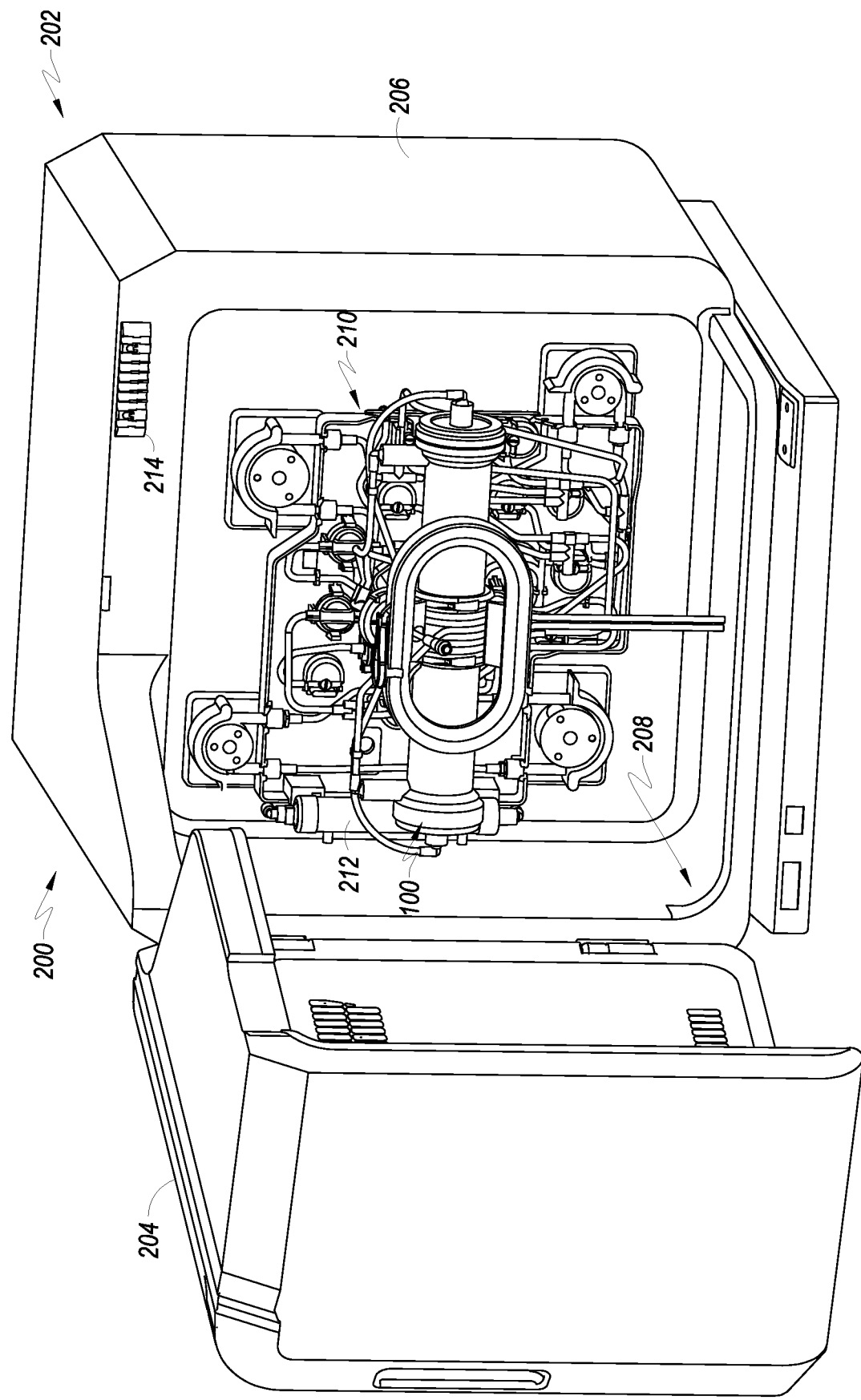
FIG. 2 illustrates a perspective view of a cell expansion system with a premounted fluid conveyance device, in accordance with embodiments.

Turning to FIG. 2, an embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210 that includes a bioreactor 100. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to embodiments.

Figure 3:
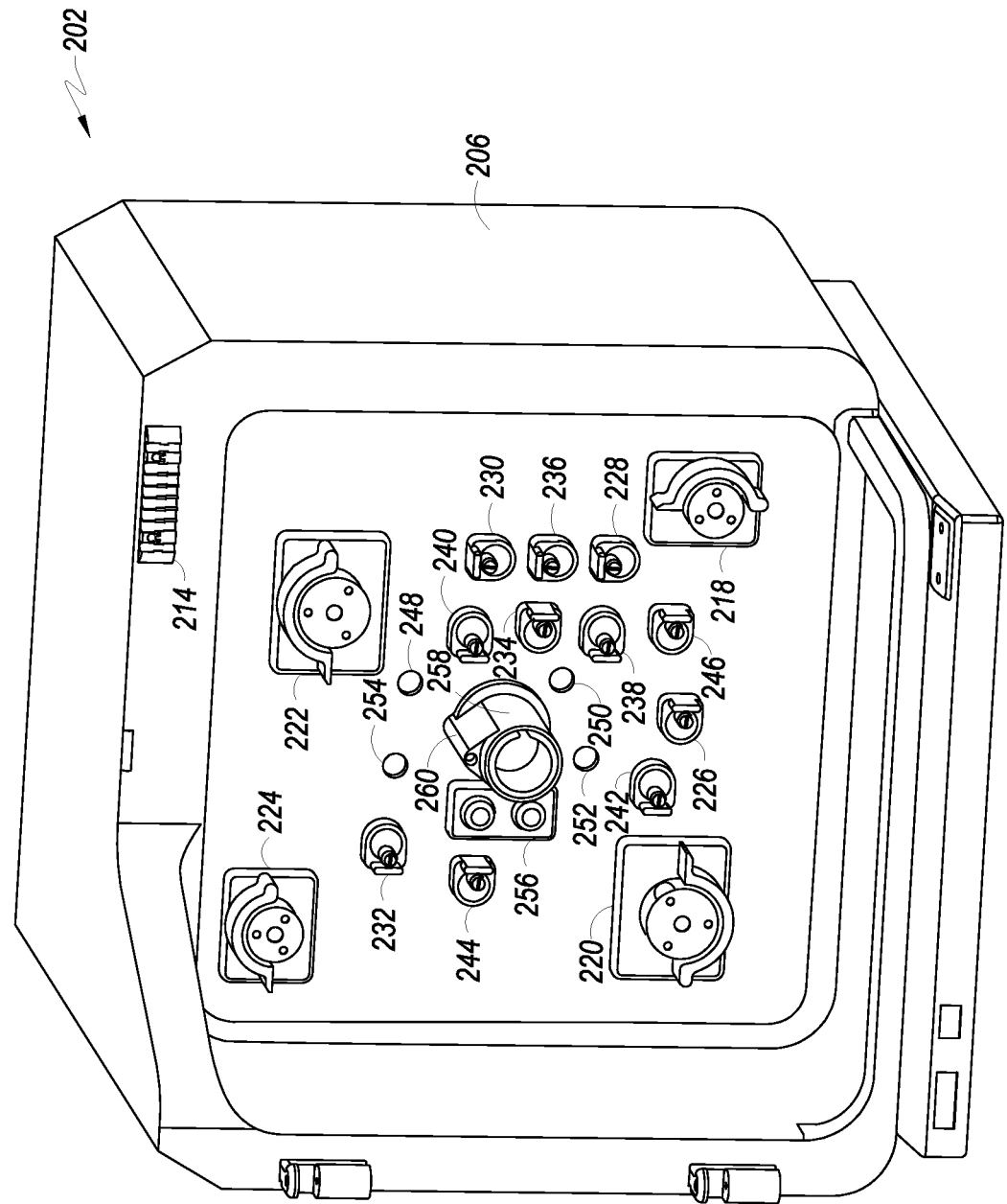
FIG. 3 depicts a perspective view of a housing of a cell expansion system, in accordance with embodiments.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with embodiments, a shaft or rocker control 258 for rotating the bioreactor 100 is shown in FIG. 3. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
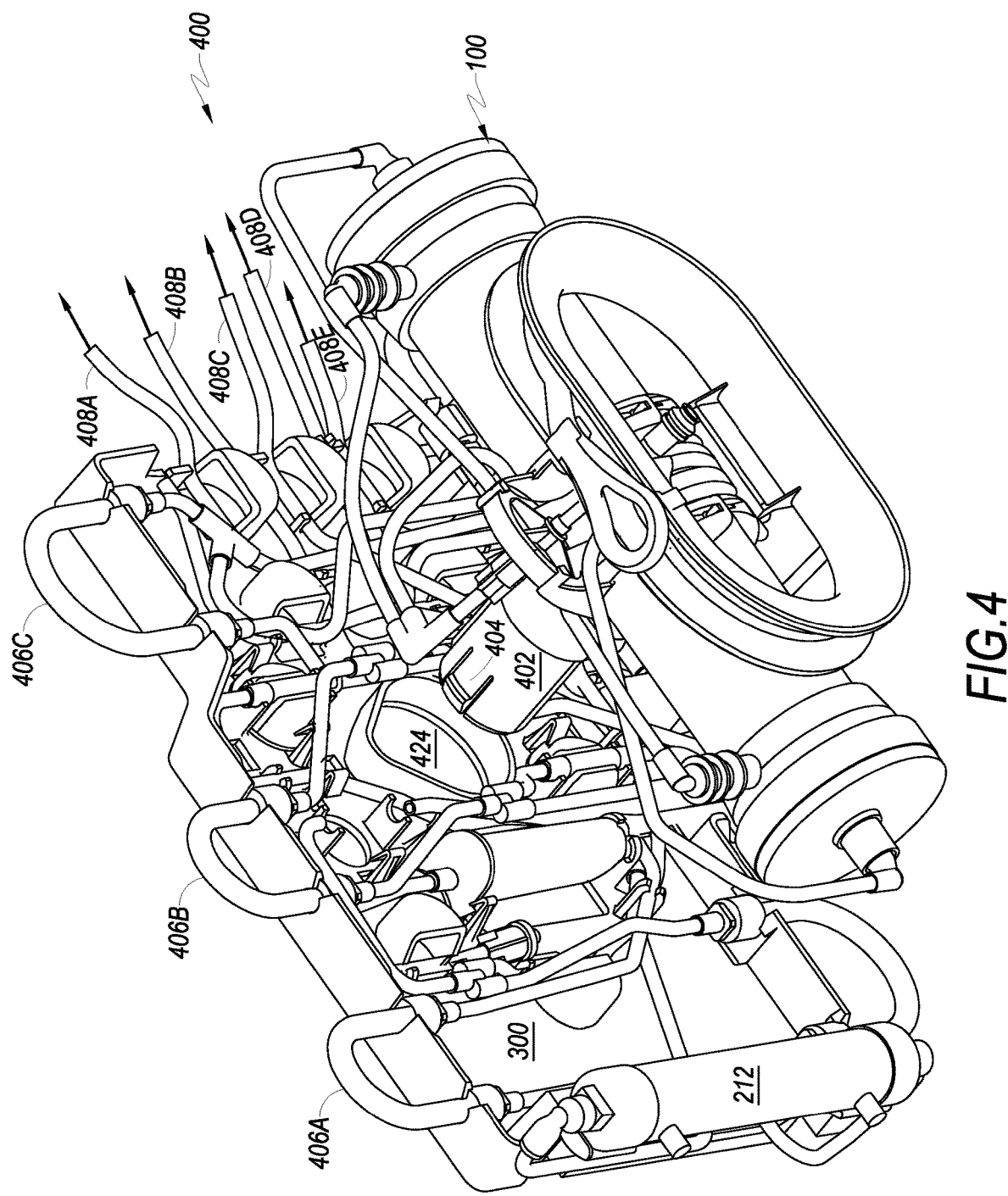
FIG. 4 illustrates a perspective view of a premounted fluid conveyance device, in accordance with embodiments.

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

In embodiments, the shaft fitting 402 and the spring member 404 connect to mechanisms of a cell expansion system that rotate the bioreactor 100. For example, in some embodiments, the cell expansion system may be part of a QUANTUM® Cell Expansion System (CES), manufactured by Terumo BCT, Inc. of Lakewood, Colo., which provides for rotation of a bioreactor. Examples of cell expansion systems that provide for rotation of the bioreactor are described in at least: U.S. Pat. No. 8,399,245, issued Mar. 19, 2013, entitled "ROTATION SYSTEM FOR CELL GROWTH CHAMBER OF A CELL EXPANSION SYSTEM AND METHOD OF USE THEREFOR;" U.S. Pat. No. 8,809,043, issued Feb. 13, 2013, entitled "ROTATION SYSTEM FOR CELL GROWTH CHAMBER OF A CELL EXPANSION SYSTEM AND METHOD OF USE THEREFOR;" and U.S. Pat. No. 9,057,045, issued Jun. 16, 2015, entitled "METHOD OF LOADING AND DISTRIBUTING CELLS IN A BIOREACTOR OF A CELL EXPANSION SYSTEM;" all three of which are hereby incorporated by reference in their entirety as if set forth herein in full.

According to embodiments, the premounted fluid conveyance assembly 400 includes tubing 408A, 408B, 408C, 408D, 408E, etc., and various tubing fittings to provide the fluid paths shown in FIGS. 5-9, as discussed below. Pump loops 406A, 406B, and 406C are also provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to embodiments.

Figure 5:
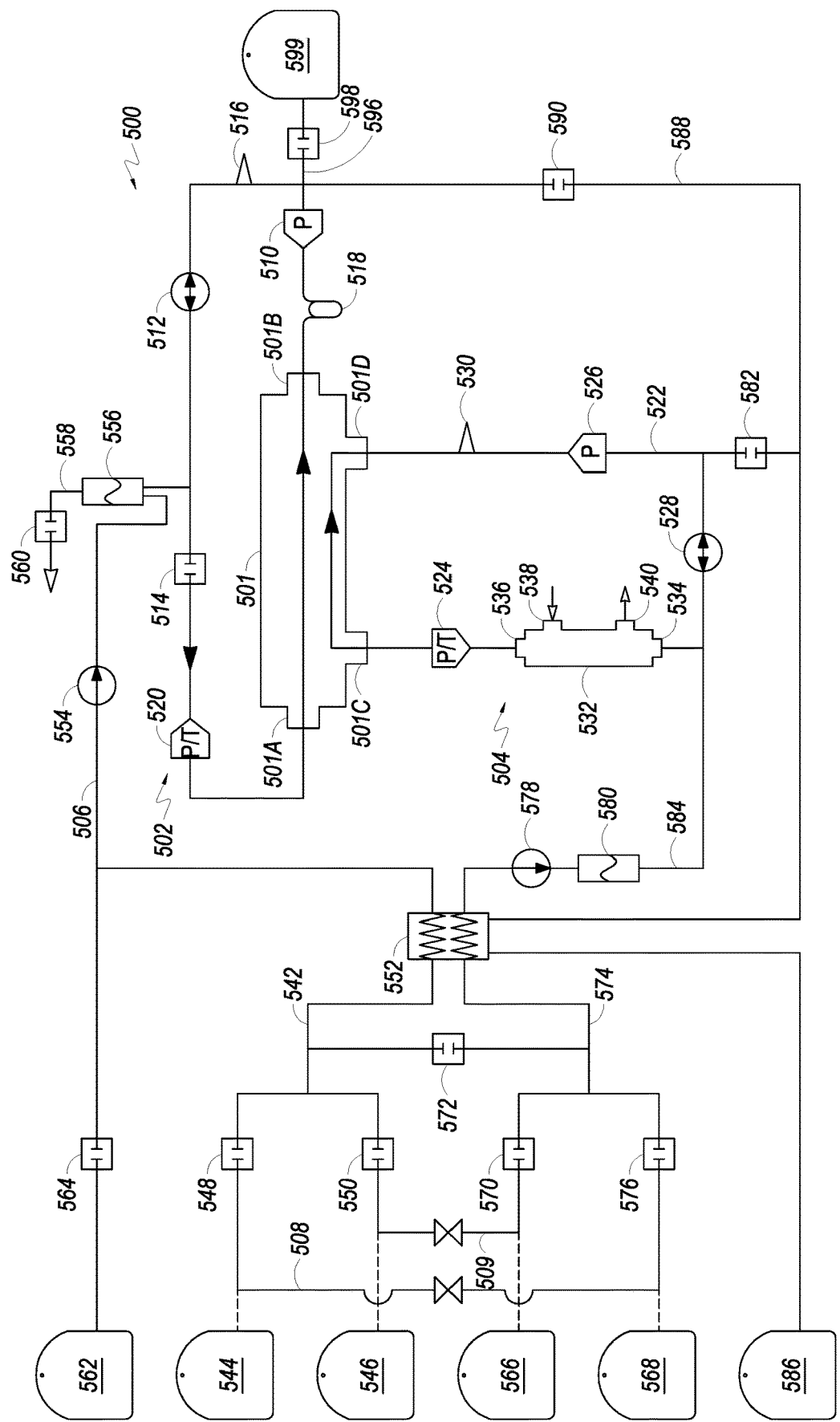
FIG. 5 depicts a schematic of a cell expansion system, in accordance with embodiments.
Figure 6:
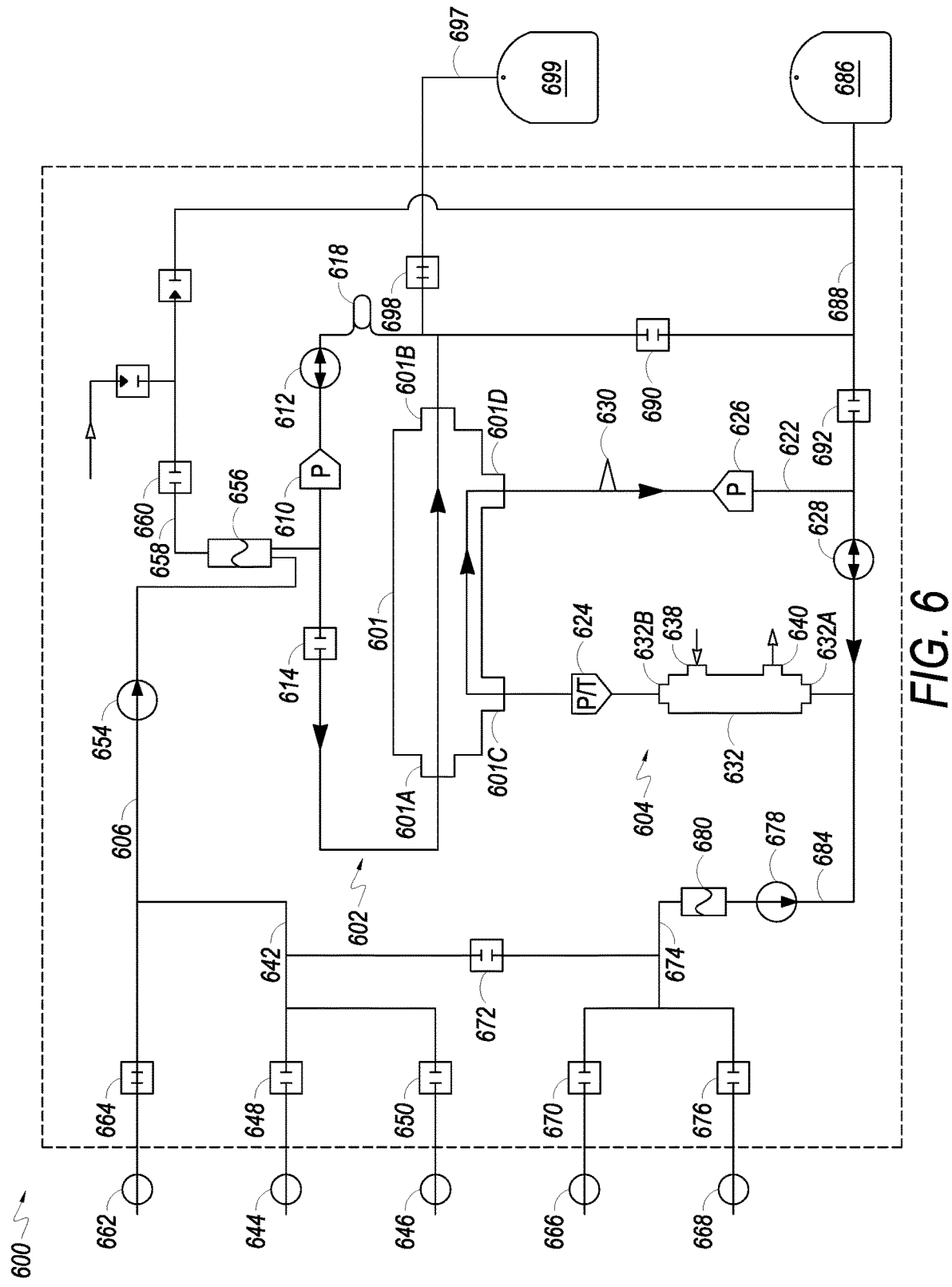
FIG. 6 illustrates a schematic of another embodiment of a cell expansion system.

FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with hollow fiber bioreactor 501 to form, at least in part, first fluid circulation path 502. Fluid flows into hollow fiber bioreactor 501 through IC inlet port 501A, through hollow fibers in hollow fiber bioreactor 501, and exits via IC outlet port 501B. Pressure gauge 510 measures the pressure of media leaving hollow fiber bioreactor 501. Media flows through IC circulation pump 512 which may be used to control the rate of media flow/rate of fluid circulation. IC circulation pump 512 may pump the fluid in a first direction (e.g., clockwise) or second direction opposite the first direction (e.g., counter clockwise). Exit port 501B may be used as an inlet in the reverse direction. Media entering the IC loop 502 may then enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in hollow fiber bioreactor 501 may be flushed out of hollow fiber bioreactor 501 into harvest bag 599 through valve 598 or redistributed within the hollow fibers for further growth. This will be described in more detail below.

Fluid in second fluid circulation path 504 enters hollow fiber bioreactor 501 via EC inlet port 501C, and leaves hollow fiber bioreactor 501 via EC outlet port 501D. Media in the EC loop 504 may be in contact with the outside of the hollow fibers in the hollow fiber bioreactor 501, thereby allowing diffusion of small molecules into and out of the hollow fibers.

Pressure/temperature gauge 524 disposed in the second fluid circulation path 504 allows the pressure and temperature of media to be measured before the media enters the EC space of hollow fiber bioreactor 501. Pressure gauge 526 allows the pressure of media in the second fluid circulation path 504 to be measured after it leaves hollow fiber bioreactor 501. With regard to the EC loop, samples of media may be obtained from sample port 530 or a sample coil during operation.

In embodiments, after leaving EC outlet port 501D of hollow fiber bioreactor 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes bubbles from media in the CES 500. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through hollow fiber bioreactor 501 in the same direction (a co-current configuration). The CES 500 may also be configured to flow in a counter-current configuration.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 548, 550, and 570. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572. An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from hollow fiber bioreactor 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with hollow fiber bioreactor 601 to form first fluid circulation path 602. Fluid flows into hollow fiber bioreactor 601 through IC inlet port 601A, through hollow fibers in hollow fiber bioreactor 601, and exits via IC outlet port 601B. Pressure sensor 610 measures the pressure of media leaving hollow fiber bioreactor 601. In addition to pressure, sensor 610 may, in embodiments, also be a temperature sensor that detects the media pressure and temperature during operation.

Media flows through IC circulation pump 612 which may be used to control the rate of media flow or rate of circulation. IC circulation pump 612 may pump the fluid in a first direction (e.g. counter clockwise) or second direction opposite the first direction (e.g., clockwise). Exit port 601B may be used as an inlet in the reverse direction. Media entering the IC loop may flow through valve 614. As those skilled in the art will appreciate, additional valves and/or other devices may be placed at various locations to isolate and/or measure characteristics of the media along portions of the fluid paths. Samples of media may be obtained from sample coil 618 during operation. Media then returns to IC inlet port 601A to complete fluid circulation path 602.

Cells grown/expanded in hollow fiber bioreactor 601 may be flushed out of hollow fiber bioreactor 601 into harvest bag 699 through valve 698 and line 697. Alternatively, when valve 698 is closed, the cells may be redistributed within hollow fiber bioreactor 601 for further growth. It is to be understood that the schematic shown represents one possible configuration for various elements of the CES 600, and modifications to the schematic shown are within the scope of the one or more present embodiments.

Fluid in second fluid circulation path 604 enters hollow fiber bioreactor 601 via EC inlet port 601C and leaves hollow fiber bioreactor 601 via EC outlet port 601D. Media in the EC loop may be in contact with the outside of the hollow fibers in the hollow fiber bioreactor 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the hollow fiber bioreactor 601. Sensor 626 allows the pressure and/or temperature of media in the second fluid circulation path 604 to be measured after it leaves the hollow fiber bioreactor 601. With regard to the EC loop, samples of media may be obtained from sample port 630 or a sample coil during operation.

After leaving EC outlet port 601D of hollow fiber bioreactor 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600.

In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through hollow fiber bioreactor 601 in the same direction (a co-current configuration). The CES 600 may also be configured to flow in a counter-current configuration.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in hollow fiber bioreactor 601, they may be harvested via cell harvest path 697. Here, cells from hollow fiber bioreactor 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. In embodiments, portions of CES 500 and 600 may be implemented by one or more features of the QUANTUM® Cell Expansion System (CES), manufactured by Terumo BCT, Inc. of Lakewood, Colo.

In one specific embodiment of using CES 600, T cells may be expanded in an embodiment of CES 600. In this embodiment, T cells, which may be collected using a leukapheresis process may be introduced into the bioreactor 601. The T cells may be introduced into the bioreactor 601 and into path 602.

In some embodiments, the T cells may be purified before introduction into bioreactor 601. The purification process may involve the use of a centrifuge and/or a purification column. Some examples of purification procedures include use of beads (e.g., functionalized beads) and/or LS columns from Miltenyi Biotec of Bergisch Gladbach, Germany.

In one embodiment, however, the T cells may be added directly to the bioreactor 601 after collection by the leukapheresis procedure without any additional purification. In some embodiments, it is believed that the growth of the T cells is enhanced by having some other cells introduced into the bioreactor with the T cells. Thus, the T cells may not be purified and be added to the bioreactor with some remaining red blood cells, platelets, granulocytes, and/or other leukocytes. In one embodiment, adding unpurified T cells may result in the expansion of mostly the T cells so that greater than about 90%, greater than about 95%, greater than about 98%, or even greater than about 99% of the cells removed from the bioreactor after expansion comprise T cells with the remaining cells including red blood cells, platelets, granulocytes, other leukocytes, and/or combinations thereof. In one embodiment, adding unpurified T cells may result in the expansion of mostly T cells so that less than about 100%, less than about 99%, less than about 98%, less than about 97%, less than about 96%, less than about 95%, less than about 94%, less than about 93%, less than about 92%, less than about 91%, or even less than about 90% of the cells removed from the bioreactor after expansion comprise T cells.

It is noted that in some embodiments, the T cells may be added to bioreactor 601, after a priming step. As may be appreciated, some T cells are not adherent and therefore it may not be required that they adhere to the hollow fiber walls of bioreactor 601 for expansion/proliferation. In these embodiments, it may be unnecessary to coat the inside of the hollow fibers with a coating to promote adhesion, e.g., fibronectin. In these embodiments, T cells (purified or unpurified) may be introduced into the bioreactor 601 after a priming step and without a bioreactor coating step.

Once in the bioreactor 601, the cells may be exposed to an activator that activates proliferation of the cells. In one example, an antigen presenting cell may have been previously grown/introduced in the bioreactor 601. In one specific embodiment, monocyte derived dendritic cells may be grown in bioreactor 601 prior to adding the T cells. In some embodiments, use of antigen presenting cells may involve a growing process that is performed initially, under conditions optimized for proliferating the antigen presenting cells.

In other embodiments, beads that are functionalized with antibodies may be added to bioreactor 601. In other embodiments, the beads may be added to a container that includes the cells, e.g., a bag with T cells, before the cells are introduced into the bioreactor. The antibodies may activate the proliferation of the T cells. One example of beads that may be used include DYNABEADS beads available from Thermo Fisher Scientific, Waltham, Mass. The beads in some embodiments may be functionalized with antibodies on their surface, some non-limiting examples of the antibodies include: anti-CD2, anti-CD3, anti-CD4, anti-CD8, anti-CD28, and anti-CD34.

In other embodiments, the activator may be in a fluid form, e.g., in a solution. The fluid with the activator may include one or more activators, such as antigens. In addition to the antigens, the fluid may include other components, some non-limiting examples including proteins, surfactants, reagents, buffers, etc. One example of a fluid that includes soluble costimulation signals is IMMUNOCULT™ Human CD3/CD28 T Cell Activator (STEMCELL Technologies Inc., Canada).

After the cells have been exposed to the activator (and during continued exposure), the cells may be expanded in bioreactor 601. During the expansion, there may be a number of materials that may be added or removed from bioreactor 601. As one example, cytokines may be used to stimulate the proliferation of the T cells. In some embodiments a single cytokine may be used, some non-limiting examples including, interleukin 2 (IL-2), interleukin 4 (IL-4), interleukin 5 (IL-5), interleukin 1 (IL-7), interleukin 15 (IL-15), and combinations thereof. In other embodiments, IL2 may be used alone or with IL-7. IL-7 may be used alone or with IL-15. In other embodiments, IL-2 may be used with IL-15. In yet other embodiments, IL-2, IL-7, and IL-15 may be used together. In some embodiments when more than one cytokine is used, the cytokines may be added individually, at the same time, at different times, or may be combined and added in combination.

It is noted that some embodiments may provide for adding cytokines more directly into the bioreactor 601, such as through port 618. In other embodiments, however, the cytokines may be added in a location, e.g., through path 606, so that the cytokines may be perfused more slowly into bioreactor 601. It is believed that in some embodiments, allowing cytokines to perfuse into bioreactor 601 may enhance T cell growth.

In addition to stimulating the T cells, they may also be fed, such as by addition of a media that may include a number of nutrients. In some embodiments, the media may be commercially available media. For example, in one embodiment, the media used to feed the T cells may be a version (modified or unmodified from the manufactured fluid) of TexMACS media available from Miltenyi Biotec of Bergisch Gladbach, Germany. In other embodiments, the media may be a version (modified or unmodified from the manufactured fluid) of CELLGRO media available from Cellgenix of Freiburg, Germany. The media may be modified by the addition of other materials, some non-limiting examples including salts, serum, proteins, etc.

As part of the expansion of the T cells, other conditions such as temperature, pH, oxygen concentration, carbon dioxide concentration, waste concentration, metabolite concentration etc. may also be controlled in bioreactor 601. In some embodiments, the flow rates of the EC side, e.g., path 604 may be used to control various parameters. For example, if it is desired to reduce waste or metabolite concentrations on the IC side, where the cells are growing, flow rate on the EC side may be increased to ensure that the waste and/or metabolites are removed from the IC side by migration through the hollow fibers from the IC side to the EC side.

After the T cells have been expanded, the cells may be removed from the bioreactor 601. The T cells may be collected in container 699.

In some embodiments, use of CES 600 may provide advantages (in growing T cells) over conventional processes. For example, the use of hollow fibers allows close cell to cell communication, which may enhance the activation and stimulation of the T cells to start and continue to proliferate. Also, the use of a hollow fiber bioreactor, such as bioreactor 601, may provide a large surface area for T cell growth, which may yield a higher concentration or higher volume of T cells.

Further, the conditions in bioreactor 601 may be controlled using a number of different components of the CES 600, including IC flow rates and EC flow rates. Also, CES 600 provides various locations for the addition of cytokines, which allows more direct, or indirect, e.g., perfusion, of cytokines into bioreactor 601.

Additionally, CES 600 provides a closed system. That is, the steps for growing the T cells may be performed without direct exposure to the ambient environment, which may contaminate the T cells, or be contaminated by the T cells or materials used in growing the T cells. It is also believed that some embodiments may provide for using a smaller starting concentration of T cells for expansion, compared to other methods/systems. In these embodiments, T cells may also be expanded to yield larger amounts than from other methods/systems.

It is also believed that some embodiments may provide for shortening the time for growing an effective dose of T cells. It is believed that yet other embodiments provide for growing T cells while utilizing less materials, such as cytokines (which may be expensive), compared to other methods/systems.

Figure 7:
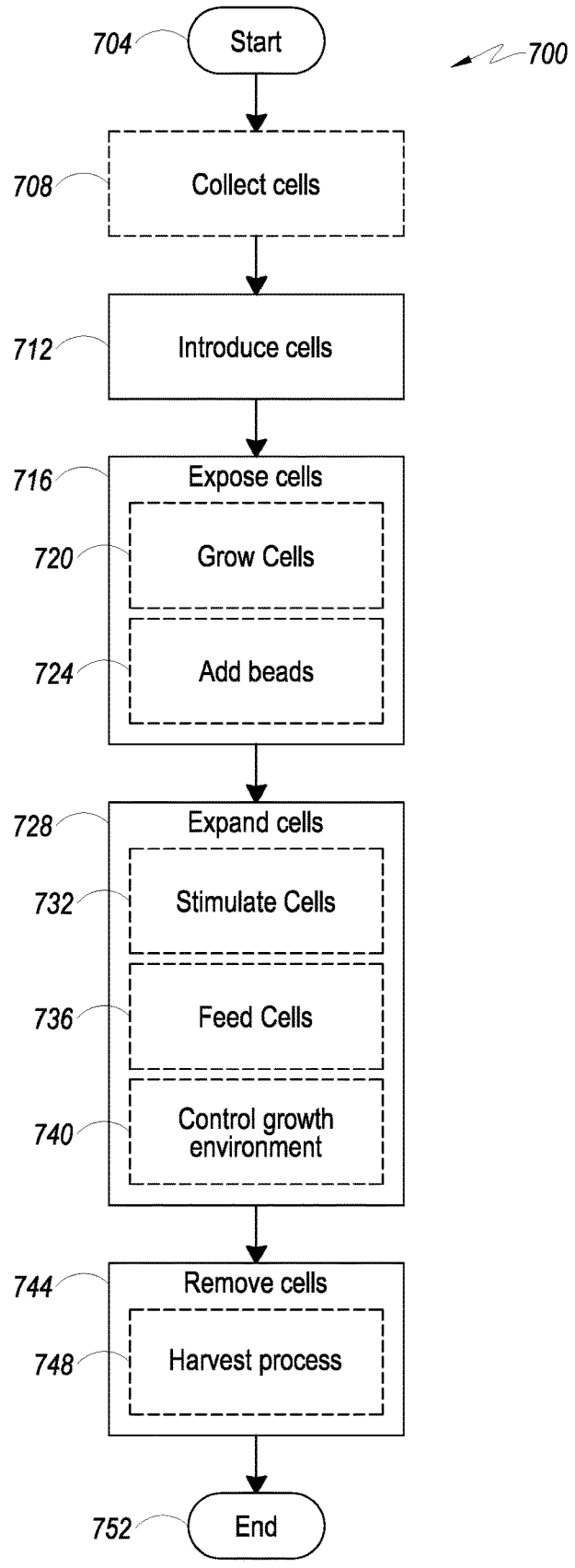
FIG. 7 illustrates a flow of a process for expanding cells according to embodiments.

FIG. 7 illustrates flow 700 that may be performed in embodiments to grow cells. Although specific devices may be described below for performing steps in flow 700, embodiments are not limited thereto. For example, some steps may be described as performed by parts of a cell expansion system or a processor, which may execute steps based on software provided as processor executable instructions. This is done merely for illustrative purposes, and flow 700 is not limited to being performed by any specific device.

Flow 700 starts at step 704 and proceeds to optional step 708 where cells may be collected. As one example, step 708 may involve an apheresis process. In one specific embodiment, a leukapheresis process is performed as part of step 708. One device capable of collecting the cells includes the COBE® Spectra Apheresis System from Terumo BCT, Inc. of Lakewood, Colo.

Flow 700 passes from step 708 to step 712, where cells may be introduced into a cell expansion system, in particular a bioreactor of a cell expansion system. As noted above, in some embodiments, flow 700 may begin at step 712. In embodiments, the bioreactor may be a hollow fiber bioreactor such as bioreactor 100 (FIG. 1). In these embodiments, step 712 may involve flowing cells into one or more individual hollow fibers. Step 712 may involve the use of a processor, pumps, valves, fluid conduit, etc. to introduce cells into a bioreactor. In one embodiment, step 712 may involve opening valves (e.g., 564, 514, 664, and/or 614) and activating pumps (e.g., 554 and 654).

After step 712, flow 700 passes to step 716 where the cells are exposed to an activator. As may be appreciated, certain cell types require activation, by for example exposure to certain proteins, before they are activated to proliferate. One example of this type of cell includes T cells. Step 716 provides for exposing cells to any necessary activator(s) that may activate the cells to expand or grow.

Step 716 may involve a number of steps that may be performed as part of step 716, or precede step 716. For example, in some embodiments, step 720 may be performed to grow an antigen presenting cell that may present the necessary activator to activate proliferation of cells. In one embodiment, step 720 may be performed prior to step 716, or even prior to step 708. In one specific example, antigen presenting cells, e.g., dendritic cells, may be grown. In these embodiments, step 720 may involve a number of steps (e.g., collecting monocytes as a precursor to the antigen presenting cells) that result in antigen presenting cells being present in the bioreactor. The surface of the antigen presenting cells, which may include major histocompatibility complex (MHC), may include antigens that when presented to other cells, e.g., T cells, may induce proliferation of the cells.

In other embodiments, step 716 may involve step 724, where beads are added to the bioreactor. As may be appreciated, in some embodiments, beads, e.g., magnetic, polymeric, glass, or ceramic beads may be modified to include on their surface specific activators for activating the proliferation of cells. As one example, magnetic beads, may be funtionalized with one or more antibodies, some non-limiting examples including, anti-CD2, anti-CD3, anti-CD4, anti-CD8, anti-CD28, and anti-CD34. When the cells are exposed to the antibodies, in the presence of other materials, the cells may be activated to proliferate. Some beads that may be suitable for use in some embodiments include DYNABEADS® beads available from Thermo Fisher Scientific, Waltham, Mass.

After step 716, flow may pass to step 728, where cells are expanded, i.e., proliferated. Step 728 may involve a number of sub-steps. For example, at sub-step 732, the cells may be stimulated for example using cytokines. The stimulation may provide for the cells to continue to proliferate.

In embodiments, step 728 may occur during a period of time of several hours, several days, or even several weeks. During this period of time, the various sub-steps (e.g., 732, 736, and/or 740) may be performed at various times during this period. For example, during the period, additional substances such as cytokines, e.g., interleukin, may be perfused or directly injected into the bioreactor to continue to stimulate proliferation of cells. Some non-limiting examples of cytokines that may be used include interleukin 1 (IL-1), interleukin 2 (IL-2), interleukin 3 (IL-3), interleukin 4 (IL-4), interleukin 5 (IL-5), interleukin 6 (IL-6), interleukin 1 (IL-7), interleukin 1 (IL-8), interleukin 1 (IL-9), interleukin 10 (IL-10), interleukin 12 (IL-12) interleukin 13 (IL-13) interleukin 15 (IL-15) interleukin 17 (IL-17) interleukin 18 (IL-18), interleukin 23 (IL-23), and combinations thereof. The cytokines may be used individually or in combination, for example, in one embodiment IL-7 may be used in combination with IL-15. In another embodiment, IL-2 and IL-7 may be used together. In yet another embodiment, IL-2 and IL-15 may be used together.

Step 728 may also involve a feeding cells step 736. Step 736 may involve adding various nutrients, including glucose, phosphates, salts, etc. Step 736 may in embodiments involve sensing a concentration of a nutrient and in response to a relatively low concentration reading, adding nutrient to the bioreactor. Step 736 may involve the use of a processor, pumps, valves, fluid conduit, etc. to add nutrients to feed the cells. Alternatively, the additions of nutrients, such as glucose may be added based on a predetermined schedule.

Step 740 may involve controlling the growth environment of the bioreactor. As may be appreciated, in addition to nutrients, the environment for optimizing growth of cells may involve a number of different parameters. For example, the temperature, pH, oxygen concentration, carbon dioxide concentration, waste concentration, metabolite concentration etc. may be monitored and controlled as part of step 740. In one specific embodiment, a flow rate of a fluid flowing through an extracapillary space (EC) side of a bioreactor may be used in controlling the pH, oxygen concentration, carbon dioxide concentration, waste concentration, metabolite concentration etc. in the intracapillary space where the cells are expanding.

Flow 700 proceeds from step 740 to step 744 where cells are removed from the bioreactor. Step 744 may involve a number of sub-steps. For example, a harvest process, which itself includes a number of steps, may be performed as part of step 744. In embodiments, step 744 may involve changing circulation rates on the intracapillary space (IC) and EC sides of the bioreactor. In other embodiments, step 744 may involve circulating various materials to ensure that any cells that may have attached themselves to the inside surface of fibers are released and removed from the bioreactor. As one example, a protease may be added to break down proteins, such as glycoproteins that may aid in binding of the cells to the fibers. Flow 700 ends at step 752.

With respect to flow 700 illustrated in FIG. 7, the operational steps depicted are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps) may be performed automatically in some embodiments, such as by a processor executing pre-programmed tasks stored in memory, in which such steps are provided merely for illustrative purposes.

Also, it is noted that although flow 700 has been described above with various steps in particular order, the present invention is not limited thereto. In other embodiments, the various steps and sub-steps may be performed in a different order, in parallel, partially in the order shown in FIG. 7, and/or in sequence as shown in FIG. 7. Also, the description above indicating that the step or sub-steps are performed by particular features or structures is not intended to limit the present invention. Rather, the description is provided merely for illustrative purposes. Other structures or features not described above may be used in other embodiments to perform one or more of the steps of flow 700. Furthermore, flow 700 may include some optional steps. However, those steps above that are not indicated as optional should not be considered as essential to the invention, but may be performed in some embodiments of the present invention and not in others.

Figure 8:
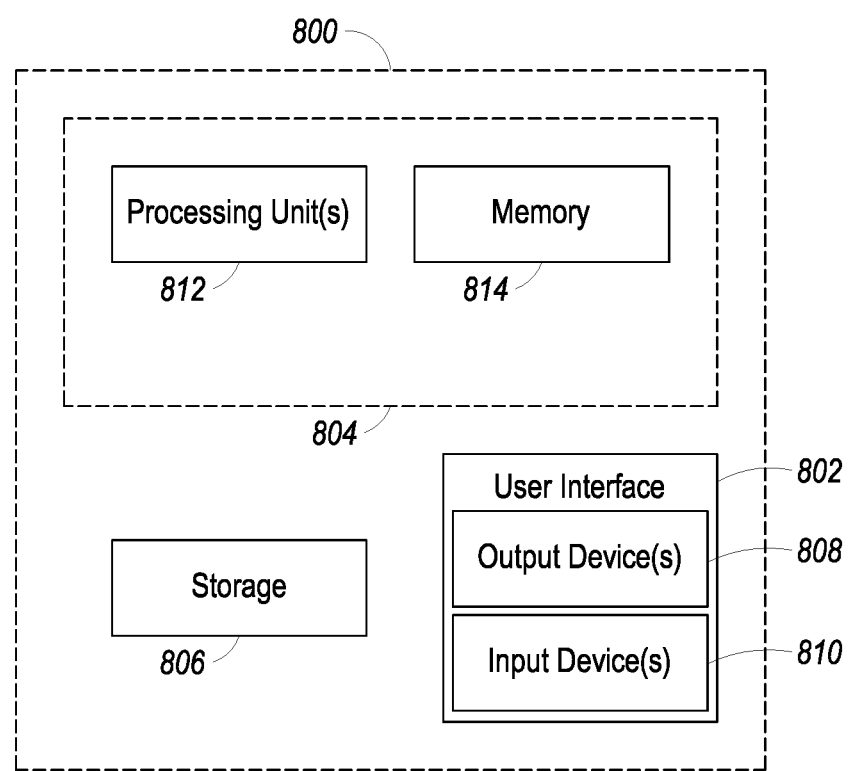
FIG. 8 illustrates components of a computing system that may be used to implement embodiments.

FIG. 8 illustrates example components of a computing system 800 upon which embodiments of the present disclosure may be implemented. Computing system 800 may be used in embodiments, for example, where a cell expansion system uses a processor to execute tasks, such as custom tasks or pre-programmed tasks performed as part of processes, such as the process illustrated by flow 700 and described above.

The computing system 800 may include a user interface 802, a processing system 804, and/or storage 806. The user interface 802 may include output device(s) 808, and/or input device(s) 810 as understood by a person of skill in the art. Output device(s) 808 may include one or more touch screens, in which the touch screen may comprise a display area for providing one or more application windows. The touch screen may also be an input device 810 that may receive and/or capture physical touch events from a user or operator, for example. The touch screen may comprise a liquid crystal display (LCD) having a capacitance structure that allows the processing system 804 to deduce the location(s) of touch event(s), as understood by those of skill in the art. The processing system 804 may then map the location of touch events to user interface (UI) elements rendered in predetermined locations of an application window. The touch screen may also receive touch events through one or more other electronic structures, according to embodiments. Other output devices 808 may include a printer, speaker, etc. Other input devices 810 may include a keyboard, other touch input devices, mouse, voice input device, etc., as understood by a person of skill in the art.

Processing system 804 may include a processing unit 812 and/or a memory 814, according to embodiments of the present disclosure. The processing unit 812 may be a general purpose processor operable to execute instructions stored in memory 814. Processing unit 812 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 814 may include any short-term or long-term storage for data and/or processor executable instructions, according to embodiments. The memory 814 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 806 may be any long-term data storage device or component. Storage 806 may include one or more of the systems described in conjunction with the memory 814, according to embodiments. The storage 806 may be permanent or removable. In embodiments, storage 806 stores data generated or provided by the processing system 804.

EXAMPLES

Some examples of methods/processes/protocols that may implement aspects of the embodiments are described below. Although specific features may be described in these examples, (cell types, cytokines, antigen presenters, etc.) they are provided merely for illustrative and descriptive purposes. The present invention is not limited to the examples provided below.

Example 1

To generate a baseline for comparison of the QUANTUM® cell expansion system (CES), monocytes elutriated from leukapheresis products are matured into dendritic cells and are combined with the donor-matched T cells (cryopreserved from leukapheresis product) following the protocol of Wölfl and Greenberg (Nature Protocols Vol. 9 No. 4, 2014), which is hereby incorporated by reference as if set forth herein in full.

Figure 9:
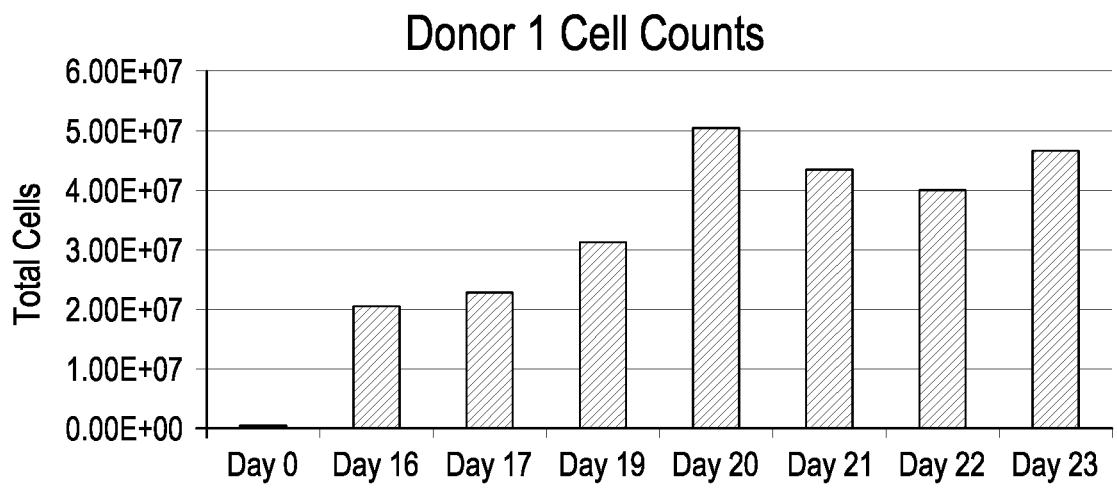
FIG. 9 illustrates a bar graph showing total cell counts at various points in time during culture, according to an embodiment.
Figure 10:
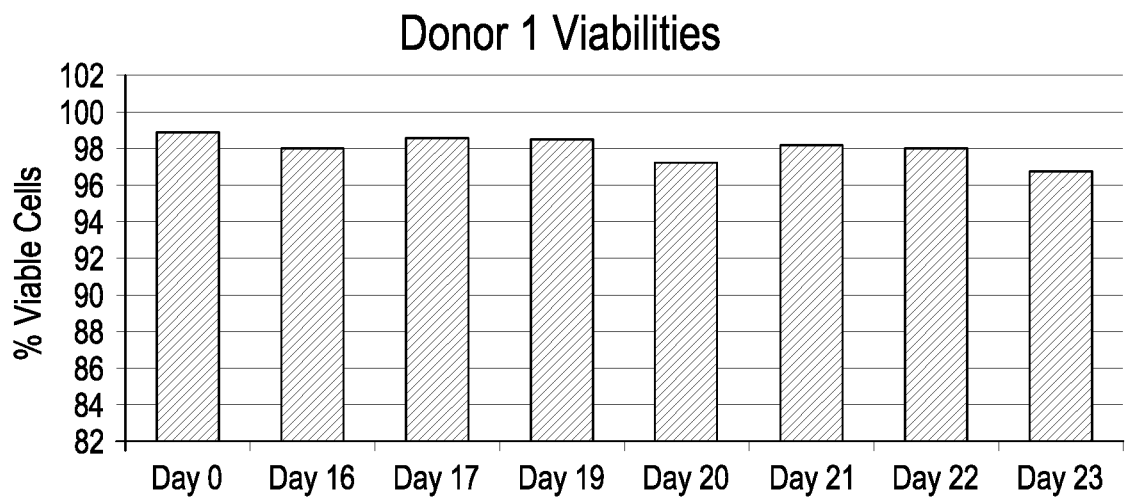
FIG. 10 illustrates a bar graph showing cell viabilities at various points in time during culture, according to an embodiment.

Donor 1 cells are cultured 23 days (5 days DC maturation and 18 days co-culture) to determine an optimal culture period. Cell expansion is observed to continue to day 20 of cell culture. After day 20, cell counts and viability decrease, as shown in FIGS. 9 and 10.

Figure 11:
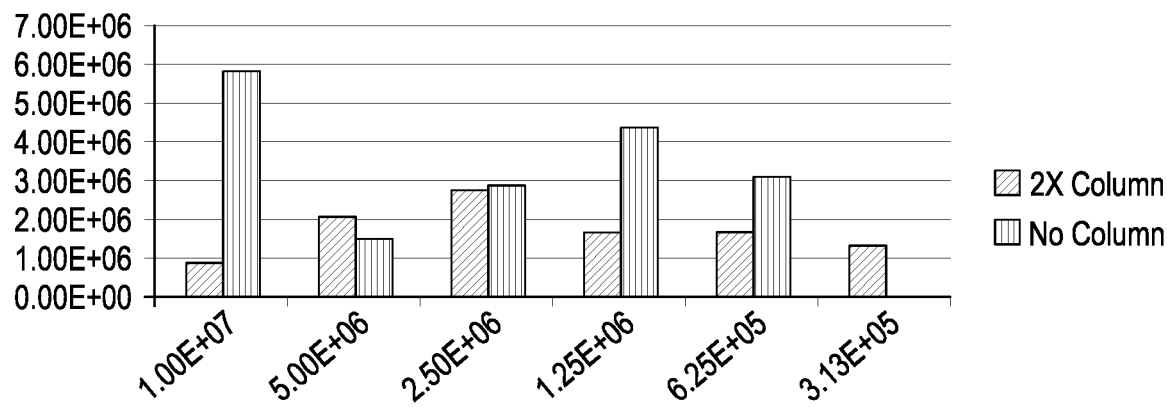
FIG. 11 illustrates a bar graph showing dendritic cell counts for purified and unpurified initial cell loadings, according to an embodiment.

Donor 2 is used to determine the optimal monocyte purity and seeding density. Monocytes are seeded onto 6 well culture plates at roughly 50% purity directly from the 5th fraction of the elutriation process and have 99% purity after magnetic bead purification using CD14 micro beads that are passed through two LS columns (Miltenyi). Both cell purity conditions are seeded starting at 10E+06 cells/mL and serial diluted two-fold down to 3.13E+05 cells/mL. The optimal seeding density for purified monocytes is observed at 2.5E+06 cells/mL and 1.25E+06 cells/mL for the unpurified cells (see FIG. 11).

Figure 12:
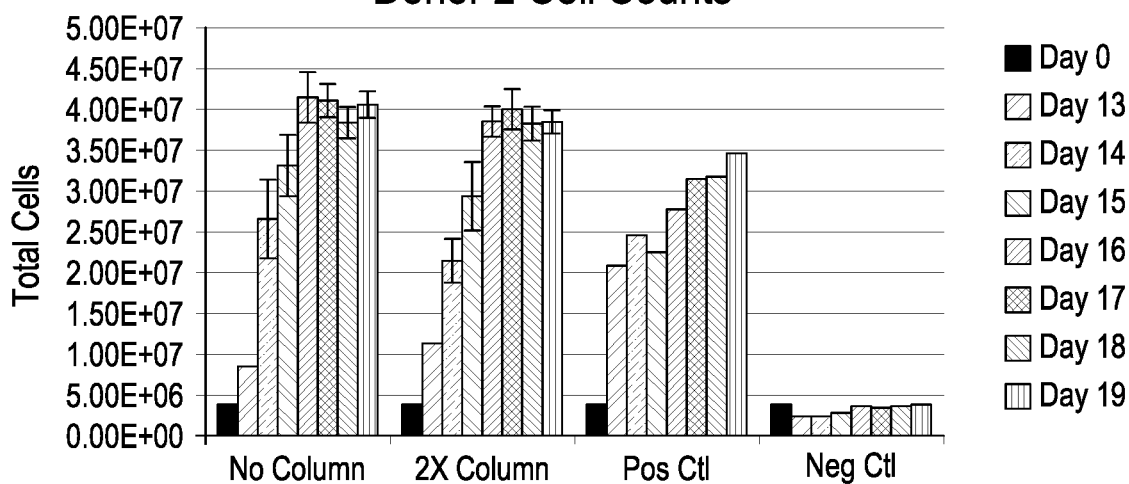
FIG. 12 illustrates a bar graph showing total cell counts at various points in time (and with various purities of initial cell loadings) during culture, according to an embodiment.
Figure 13:
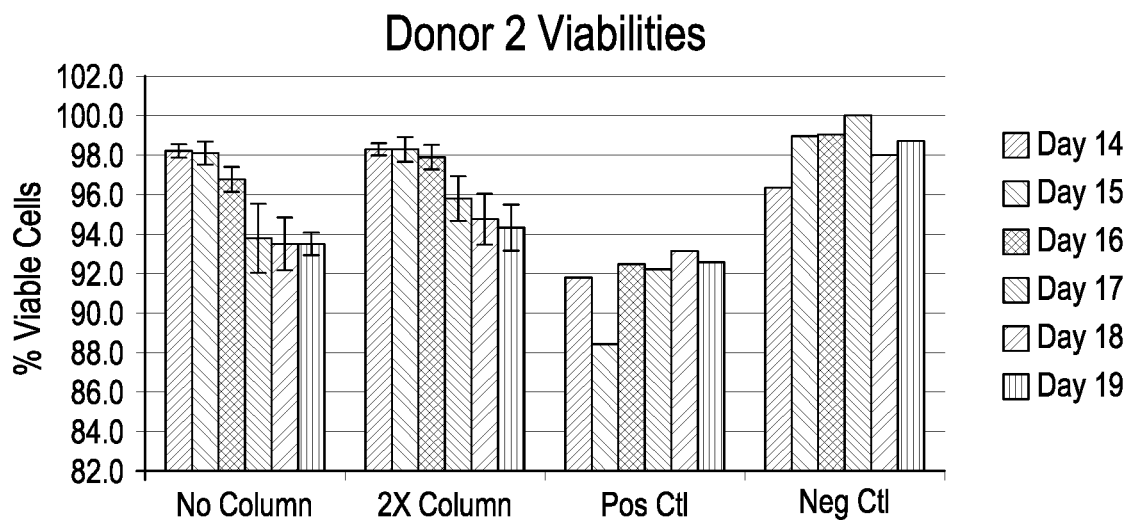
FIG. 13 illustrates a bar graph showing cell viabilities at various points in time (and with various purities of initial cell loadings) during culture, according to an embodiment.

Monocyte derived dendritic cells are pooled by condition prior to co-culture with T cells. T cells are co-cultured with monocyte derived dendritic cells at a ratio of 4:1 and are cultured 19 days. Cells directly from the elutriation process are observed to perform just as well, if not better, at expanding T cells when compared to purified monocytes (see FIG. 12). As with the first donor, cell viabilities may decrease as cell expansion starts to level off (see FIG. 13).

Example 2

Figure 14:
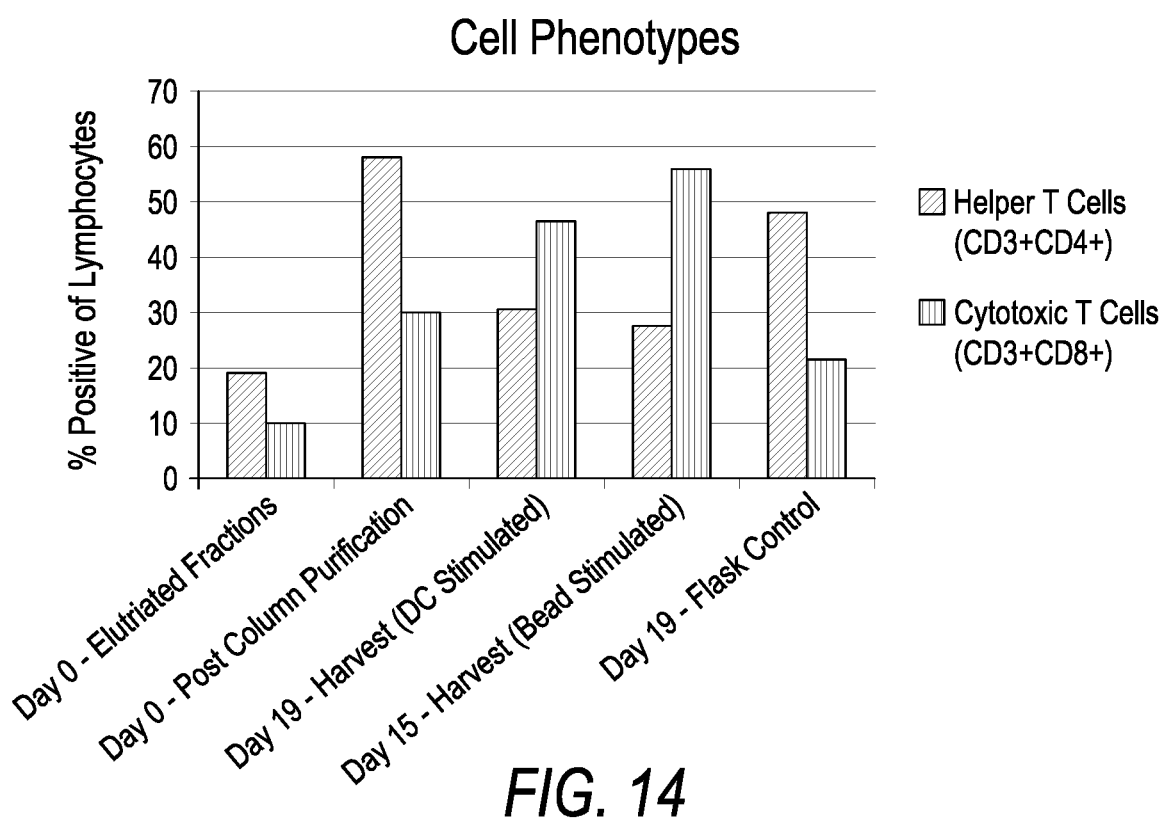
FIG. 14 illustrates a bar graph showing cell phenotype distribution, according to an embodiment.

T cells are successfully expanded in the QUANTUM® CES via two strategies: costimulation of CD3 and CD28 by antibody-functionalized paramagnetic beads (DynaBeads T cell Activator) (Q1070), and antigen presentation by monocyte-derived dendritic cells (DCs) (Q1069), which are professional antigen-presenting cells (APCs) matured from monocytes present in the original leukapheresis product. Both of these approaches show initial promise in QUANTUM® CES for the expansion of T cell cultures (see FIG. 14).

Figure 15:
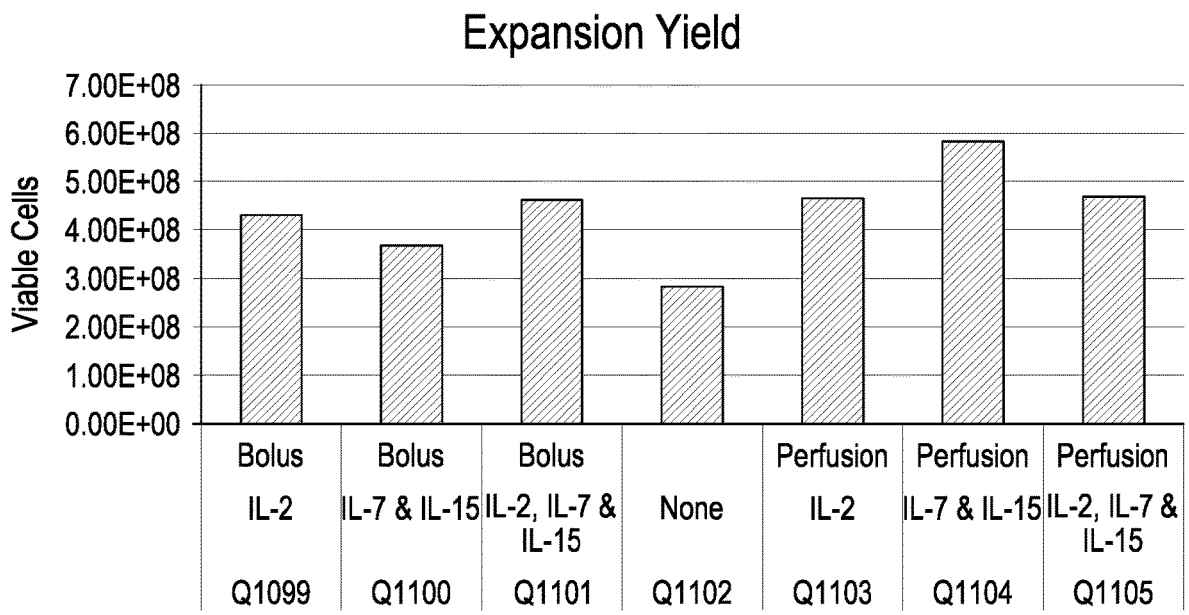
FIG. 15 illustrates a bar graph comparing various cytokine combinations and delivery methods, according to an embodiment.

FIG. 15 shows the phenotypic distribution of cells expanded in the QUANTUM system for proof-of-concept. For both the DC and bead stimulated expansions a shift is observed in the phenotype distribution (CD4:CD8 ratio) from both the starting product and the cells expanded in T175 flasks. Regardless of stimulation method this early data suggests the QUANTUM® CES favors CD8 T cell expansion.

Table 1 below shows the number of cells loaded and the number of cells harvested from the proof of concept runs.

TABLE 1

T CELL EXPANSION IN QUANTUM ® CES

| Name | Condition | T Cells Loaded | Cells Harvested | Fold Expansion |
|---|---|---|---|---|
| Q1069 | DC-Stimulation | $6.32 \times 10^7$ | $6.96 \times 10^8$ | 11.01 |
| Q1070 | Bead-Stimulation | $9.44 \times 10^7$ | $8.54 \times 10^8$ | 9.05 |

Example 3

Numerous cytokines aid T cell expansion, including IL-2, and the combination IL-7 and IL-15. The two candidate methods for the delivery of these cytokines are bolus injection and continual perfusion of pre-formulated medium containing appropriate cytokine concentrations. This is explored with a 7 arm study in which IL-2 alone, IL-7 and IL-15 together and the combination of all three cytokines are fed into the QUANTUM® CES by the two methods mentioned earlier for a direct comparison. The control for that study is one arm with no cytokines. From this exploration, it is observed that a greater fold expansion is gained from the perfusion of IL-7 and IL-15 together (see FIG. 15). FIG. 15 illustrates the harvest yield of QUANTUM® CES runs comparing cytokine combinations and delivery vehicles.

Example 4

Figure 16:
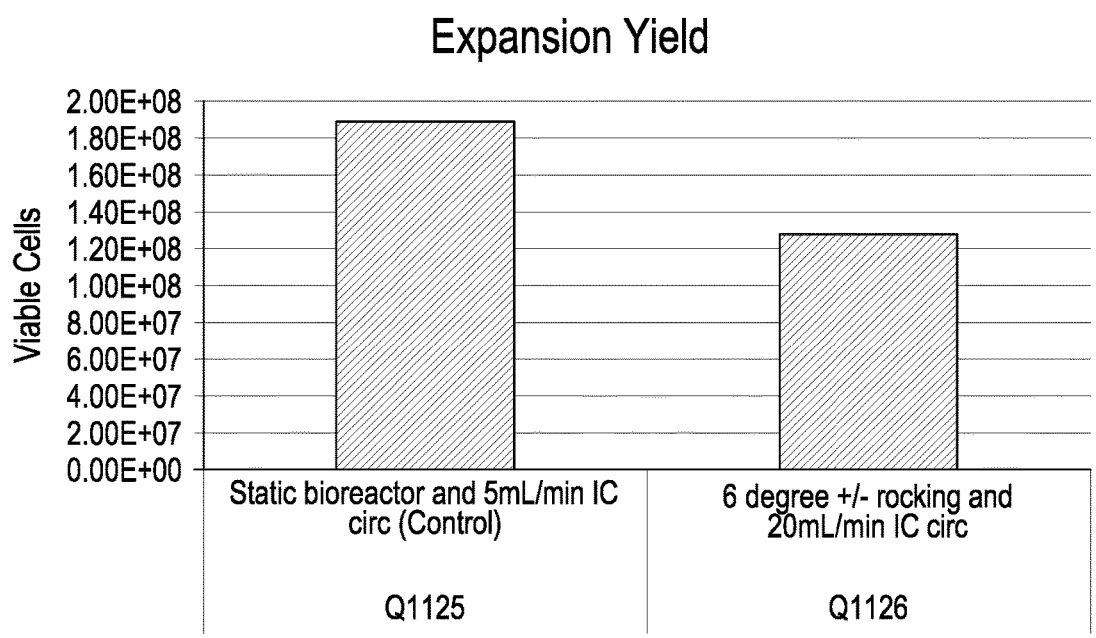
FIG. 16 illustrates a bar graph showing cell viabilities under different circulation rates and reactor movement, according to an embodiment.

Our next step is to investigate increasing the IC circulation rate and adding a 6 degree rocking motion to the bioreactor during cell expansion. We found that these new conditions to the culture environment had a negative effect on T cell expansion (see FIG. 16). FIG. 16 illustrates a graph showing harvest yield comparisons of a control (static bioreactor; 5 ml/min circulation) vs. increased IC circulation with rocking (+/−6 degrees rocking; 20 ml/min circulation).

Example 5

T-cell expansion is facilitated with TexMACS GMP grade media (Miltenyi Biotec GmbH, Germany) supplemented with recombinant human interleukin 2 improved sequence (IL-2 IS) (Miltenyi Biotec GmbH, Germany) and recombinant human interleukin 7 (IL-7) (Miltenyi Biotec GmbH, Germany). T-cell expansion is initiated using bound costimulation signals, DynaBeads® Human T-Activator CD3/CD28 (Life Technologies, Grand Island, N.Y.) or soluble costimulation signals, ImmunoCult™ Human CD3/CD28 T Cell Activator (STEMCELL Technologies Inc., Canada). The QUANTUM® CES (Terumo BCT, Lakewood, Colo.) is primed with phosphate buffered saline (PBS) (Lonza, Switzerland) to remove any air from the system. Following the priming sequence, PBS is exchanged with TexMACS GMP media.

Fresh normal peripheral blood leukapheresis products (LeukoPak) is obtained from single donors (AllCells, LLC, Alameda, Calif. and HemaCare Corp, Van Nuys, Calif.) using a COBE® Spectra Apheresis System (Terumo BCT, Lakewood, Colo.). Upon arrival in the lab, cell concentration and viability is determined by the Vi-Cell XR Cell Viability Analyzer (Beckman Coulter Inc, Brea, Calif.) and the percentage of lymphocytes is quantified on Coulter Ac-T diff2 (Beckman Coulter Inc, Brea, Calif.) hematology analyzer.

Aliquots of $1.0 \times 10^8$ lymphocytes from the leukapheresis product is combined with DynaBeads® in a 2:1 cell to bead ratio or ImmunoCult™ at 2.5 μl/$1.0 \times 10^6$ lymphocyte and $1.0 \times 10^5$ IU IL-2 and $2.5 \times 10^3$ ng IL-7 and brought up to volume of 100 mL in TexMACS GMP media in a sterile storage bottle. The cell/cytokine/stimulation vector solutions are then processed into a Cell Inlet Bag (Terumo BCT, Lakewood, Colo.) and loaded on the IC side of the bioreactor with media circulation to achieve a uniform distribution of the solution among the hollow fibers.

After cell load, TexMACS media is circulated 1 mL/min on the IC side and 100 mL/min on the EC side with a continuous perfusion of media with IL-2 (200 IU/mL) and IL-7 (5 ng/mL) at 0.1 mL/min at the IC inlet of the bioreactor. Bioreactor orientation is static at 0° through the first 6 days of expansion except on days 3, 6, and 9 when a bolus addition of 150 mL of media with IL-2 and IL-7 (DynaBeads® expansions) or 150 mL of media with IL-2 and IL-7 and soluble costimulation signal (ImmunoCult™ expansions) is added to the IC side of the bioreactor at 30 mL/min while the IC and EC circulation is set to 100 mL/min each, and the bioreactor is in motion with continuous swing from −90° to 180° with a 1 second dwell in between. Once bolus addition is completed, the bioreactor is returned to a static 0° and inlet and circulations pump settings returned to the values stated for the start of expansion.

Starting on day 6 the bioreactor is flipped 180° every 24 hours between 0° and 180°. IL-2 and IL-7 concentrations in bolus additions vary for each addition, see Table 2. After each bolus addition, when the cells are in a uniform suspension a portion of the IC sample loop is spliced off using TSCD® II Sterile Tubing Welder (Terumo BCT, Lakewood, Colo.). This sample is used to monitor cell concentration, viability, cell phenotype and secreted cytokines over the course of expansion.

TABLE 2

BOLUS ADDITION VALUES
Bolus Additions

| | Volume (mL) | IL-2 (IU) | IL-7 (ng) |
|---|---|---|---|
| Day 0 (cell load) | 100 | 1.00E+05 | 2.50E+03 |
| Day 3 | 150 | 2.00E+05 | 5.00E+03 |
| Day 6 | 150 | 2.00E+05 | 5.00E+03 |
| Day 9 | 150 | 4.00E+05 | 1.00E+04 |

Cells are harvested from the QUANTUM® CES on days 7, 10, or 12 of expansion using the High Density Washout automated task. To facilitate this method of harvest, media is circulated on the IC side of the bioreactor for five (5) minutes at a rate of 100 mL/min with the bioreactor in motion (with continuous swing from −90° to 180° with a 1 second dwell in between) to achieve a well mixed cell suspension. After media circulation the harvest bag is welded onto the waste line in place of the waste bag. Task settings for the High Density Washout are set to the following: IC Inlet=200 mL/min, EC circulation=300 mL/min and Stop condition=1000 mL. Media without cytokine is used for this task. After harvest cells are assayed for viability and absolute count and phenotype characterization by flow cytometry.

Cells are characterized as T-cells by the expression of CD3 and helper and cytotoxic subsets are characterized by the expression of CD4 and CD8 respectively. The UCHT1 clone for CD3 conjugated to PerPC-Cy5.5 (BD Biosciences, San Jose, Calif.) is used to stain both surface and intracellular CD3 receptors in the samples. The SK3 clone of CD4 conjugated to PE (BD Biosciences, San Jose, Calif.) is used to stain surface CD4 receptors in the samples. The BW135/80 clone of CD8 conjugated to VioBright FITC (Miltenyi Biotec GmbH, Germany) is used to stain surface CD8 receptors in samples. Non-viable cells are discriminated from analysis using an eFluor®780 Fixable Viability Dye (eBioscience, San Diego, Calif.). Surface and intracellular staining for the cells is done using the FIX & PERM® Cell Permeabilization Kit (Life Technologies, Grand Island, N.Y.). Samples are acquired on a FACSCanto II (BD Biosciences, San Jose, Calif.) and analyzed using FACSDiva software v6.1.3 (BD Biosciences, San Jose, Calif.). FACSCanto II is calibrated using BD FACSDiva CS&T Beads (BD Biosciences, San Jose, Calif.) and compensation is calculated using BD CompBeads (BD Biosciences, San Jose, Calif.) and ArC™ Amine Reactive Compensation Bead Kit (Life Technologies, Grand Island, N.Y.). 10,000 events are recorded per sample.

Samples are taken from the IC and EC sides of the bioreactor periodically during maturation and stored at −20° C. Samples are later thawed at room temperature and assayed for IL-2, IL-4, IL-5, IL-9, IL-10, IL-13, IL-17 and IFNγ using a Th1/Th2/Th17 Human Magnetic 8-Plex Panel for Luminex™ Assay (Life Technologies, Grand Island, N.Y.). The assay is analyzed using a MAGPIX Analyzer (Luminex, Austin, Tex.) running xPONENT (Luminex, Austin, Tex.) acquisition and analysis software.

Figure 17:
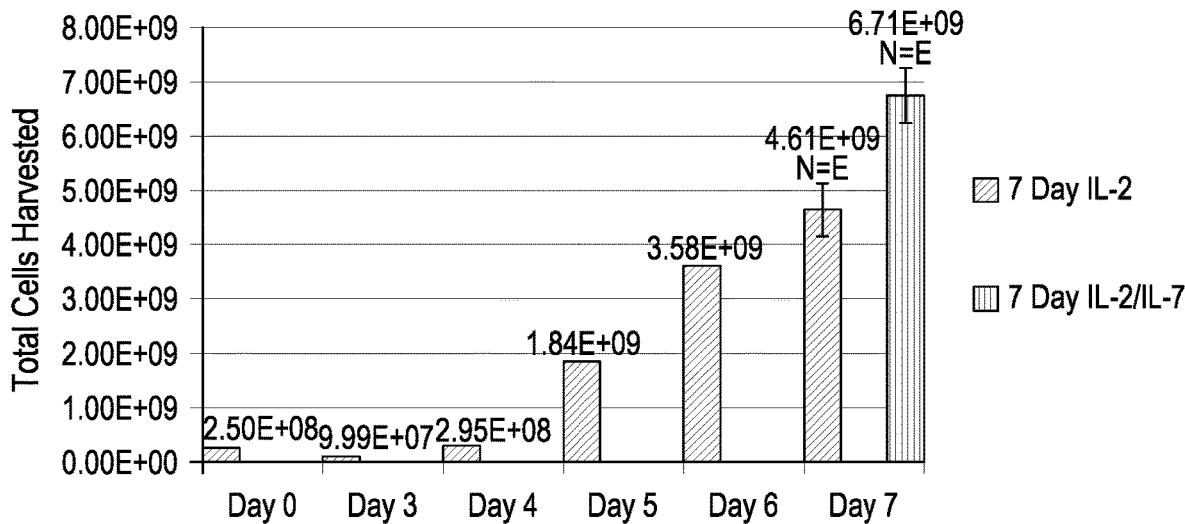
FIG. 17 illustrates a bar graph showing total cells harvested at various points in time during culture with different combinations of cytokines, according to an embodiment.
Figure 18:
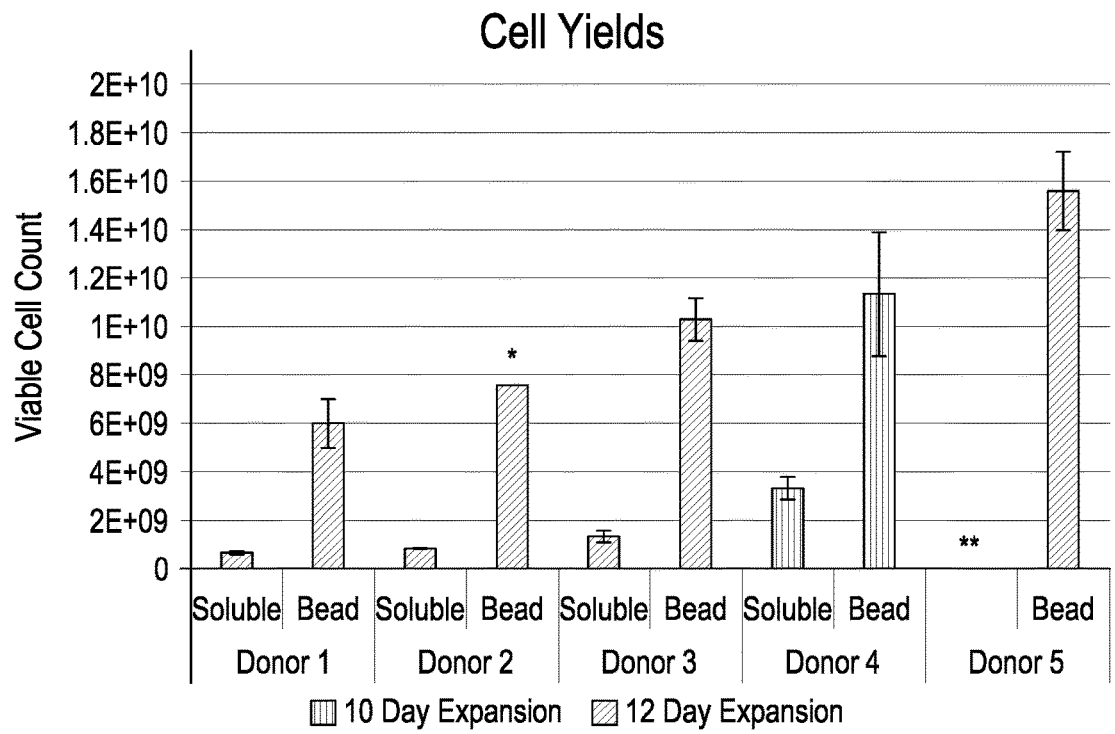
FIG. 18 illustrates a bar graph showing cell yields using different activators, according to an embodiment.
Figure 19:
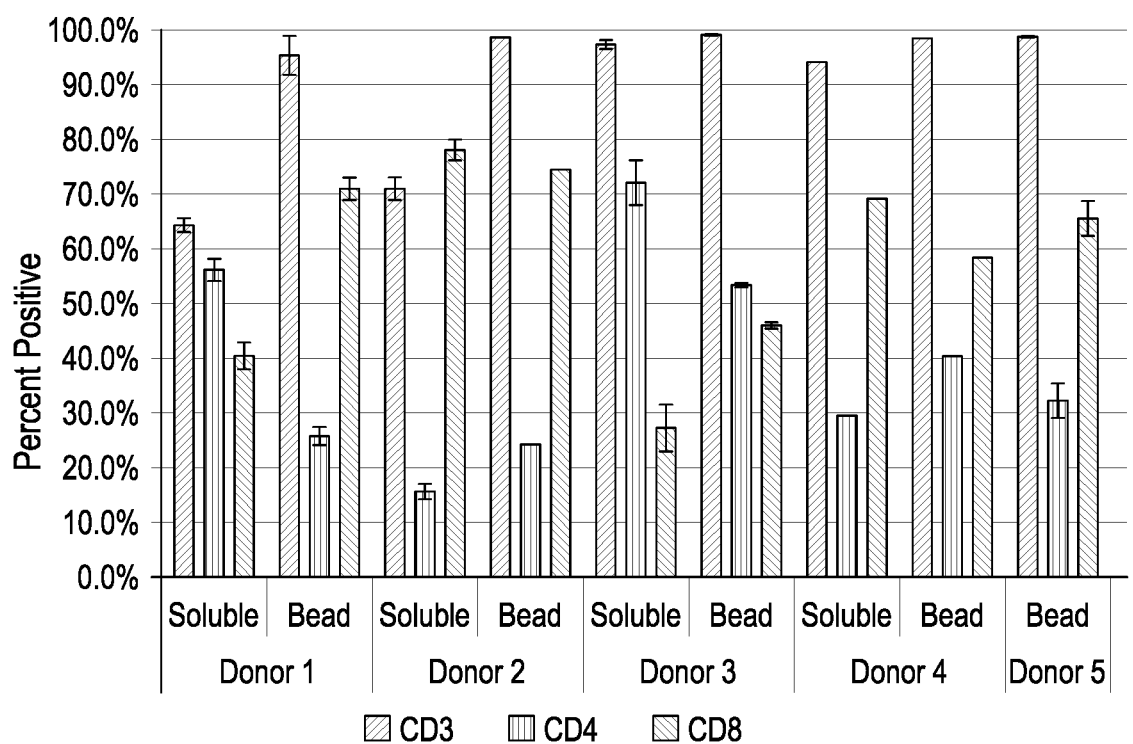
FIG. 19 illustrates a bar graph showing cell phenotypes using different activators, according to an embodiment.
Figure 20:
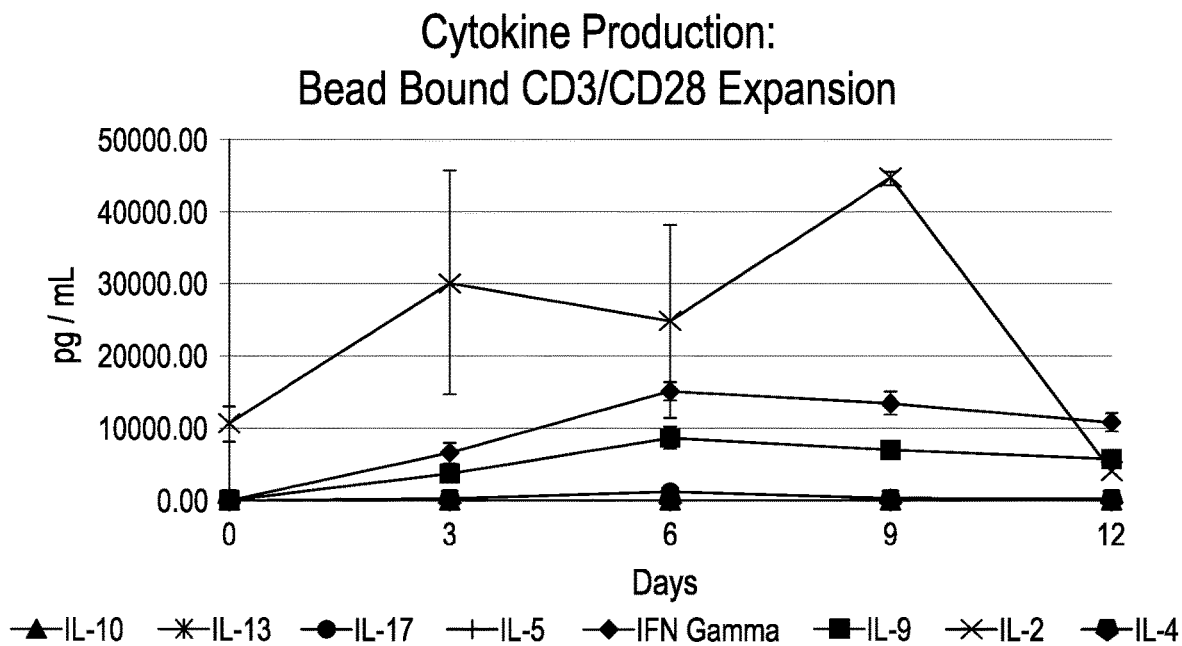
FIG. 20 illustrates a graph showing cytokine production, according to an embodiment.
Figure 21:
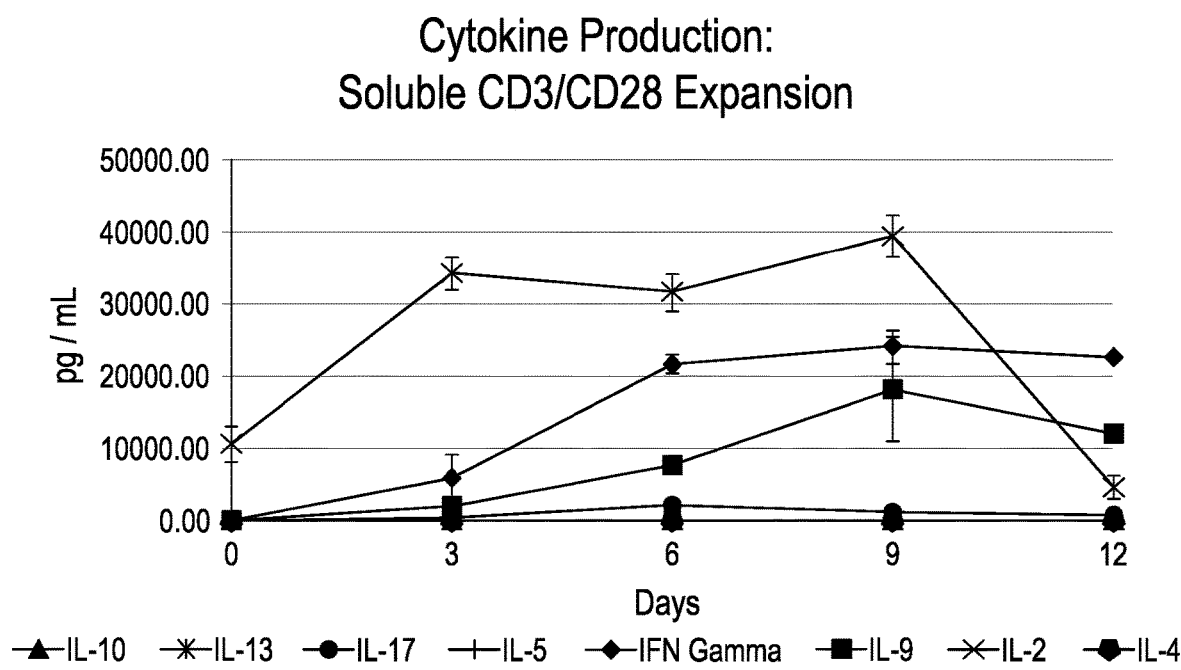
FIG. 21 illustrates a graph showing cytokine production, according to another embodiment.

The use of IL-7 in conjunction with IL-2 shows a significant increase in T-cell expansion over IL-2 alone in the QUANTUM® CES, see FIG. 17. T-cell expansion in the QUANTUM® CES using bead bound CD3 and CD28 co-stimulatory antibodies is shown to be superior to soluble co-stimulation antibodies in our experiments in the QUANTUM® CES, see FIG. 18. Expansion product after 7 days is consistently about 95% CD3+ cells in bead bound expansions with similar percentages in most soluble based expansions, see FIG. 19. Viability of the cell product after expansion is consistently better in the bead bound expansions vs. the paired soluble expansion across all donors, see Table 3 below. In Table 3, * denotes that data was not available for those expansions due to contamination of the system.  denote that analysis was done on the corresponding paired expansion. Cytokine analysis of all experiments show an increase in cytokines associated with Th1 and cytotoxic subsets, with an increase in IL-9, which has been known to stimulate cell proliferation and prevent apoptosis, attributed to stimulation of the IL-2 receptor family by the addition of IL-7 to the culture media, see FIG. 20 & FIG. 21.

The QUANTUM® CES may expand T-cells over 500 fold from a fraction of an apheresis blood collection. The manufacturing process control of an automated and functionally closed system may help reduce the labor and open events involved in T-cell maturation, which may result in more efficient production of a cellular product.

TABLE 3

EXPANSION DATA

| Source | CD3/CD28 | Expn. (Days) | Lymphcyts Loaded | % CD3+ Cells Loaded | Cells Hrvstd. | Viability of Hrvst. | % CD3+ Cells Hrvstd | % CD4+ of CD3+ Cells Hrvstd | % CD8+ of CD3+ Cells Hrvstd | Fold Expn. | Dbl. Time (hrs) | Avrg. Fold Expn. | Avrg. Dbl. Time |
|---|---|---|---|---|---|---|---|---|---|---|---|---|---|
| Donor 1.1 | Soluble | 11.9 | 1.00E+08 | 66.11% | 6.31E+08 | 59.1% | 65.4% | 53.5% | 43.0% | 9.55 | 88.70 | 10.46 | 84.83 |
| Donor 1.2 | Soluble | 11.9 | 1.00E+08 | 66.11% | 6.88E+08 | 61.1% | 63.9% | 56.8% | 39.4% | 10.41 | 84.50 | | |
| Donor 1.3 | Soluble | 11.9 | 1.00E+08 | 66.11% | 7.55E+08 | 60.0% | 62.9% | 57.3% | 38.5% | 11.41 | 81.30 | | |
| Donor 1.4 | Bead | 11.9 | 1.00E+08 | 66.11% | 4.86E+09 | 80.6% | 96.0% | 24.0% | 73.3% | 73.53 | 46.10 | 90.53 | 44.07 |
| Donor 1.5 | Bead | 11.9 | 1.00E+08 | 66.11% | 6.58E+09 | 83.7% | 97.7% | 27.1% | 70.2% | 99.56 | 43.00 | | |
| Donor 1.6 | Bead | 11.9 | 1.00E+08 | 66.11% | 6.51E+09 | 84.1% | 90.9% | 26.7% | 69.4% | 98.50 | 43.10 | | |
| Donor 2.1 | Soluble | 11.9 | 1.00E+08 | 18.16% | 8.89E+08 | 61.5% | 68.9% | 17.0% | 76.0% | 48.93 | 50.90 | 47.24 | 51.37 |
| Donor 2.2 | Soluble | 11.9 | 1.00E+08 | 18.16% | 8.23E+08 | 69.3% | 70.7% | 15.0% | 78.4% | 45.30 | 51.90 | | |
| Donor 2.3 | Soluble | 11.9 | 1.00E+08 | 18.16% | 8.62E+08 | 64.3% | 73.0% | 14.3% | 79.7% | 47.47 | 51.30 | | |
| Donor 2.4 | Bead | 11.9 | 1.00E+08 | 18.16% | *** | *** | *** | *** | *** | *** | *** | 415.64 | 32.80 |
| Donor 2.5 | Bead | 11.9 | 1.00E+08 | 18.16% | 7.55E+09 | 85.3% | 98.6% | 24.3% | 74.5% | 415.64 | 32.80 | | |
| Donor 2.6 | Bead | 11.9 | 1.00E+08 | 18.16% | *** | *** | *** | *** | *** | *** | *** | | |
| Donor 3.1 | Soluble | 13 | 1.00E+08 | 41.65% | 1.43E+09 | 75.3% | 97.3% | 67.5% | 31.9% | 34.33 | 61.10 | 32.65 | 62.40 |
| Donor 3.2 | Soluble | 13 | 1.00E+08 | 41.65% | 1.08E+09 | 66.8% | 96.1% | 75.0% | 24.0% | 25.93 | 66.50 | | |
| Donor 3.3 | Soluble | 13 | 1.00E+08 | 41.65% | 1.57E+09 | 76.5% | 97.8% | 73.7% | 25.6% | 37.70 | 59.60 | | |
| Donor 3.4 | Bead | 13 | 1.00E+08 | 41.65% | 9.29E+09 | 86.3% | 98.9% | 52.8% | 46.4% | 223.05 | 40.00 | 247.22 | 39.27 |
| Donor 3.5 | Bead | 13 | 1.00E+08 | 41.65% | 1.07E+10 | 91.1% | 98.8% | 53.4% | 45.5% | 256.90 | 39.00 | | |
| Donor 3.6 | Bead | 13 | 1.00E+08 | 41.65% | 1.09E+10 | 87.7% | 99.2% | 53.0% | 46.2% | 261.70 | 38.80 | | |
| Donor 4.1 | Soluble | 9.8 | 1.00E+08 | 65.30% | 3.00E+09 | 83.1% | ** | ** | ** | 45.94 | 42.60 | 50.92 | 41.55 |
| Donor 4.2 | Soluble | 9.8 | 1.00E+08 | 65.30% | 3.65E+09 | 80.2% | 94.2% | 29.5% | 68.9% | 55.90 | 40.50 | | |
| Donor 4.3 | Bead | 10.8 | 1.00E+08 | 165.30% | 9.53E+09 | 82.1% | ** | ** | ** | 57.64 | 32.70 | 53.42 | 31.75 |
| Donor 4.4 | Bead | 11.8 | 1.00E+08 | 265.30% | 1.31E+10 | 82.9% | 98.3% | 40.30% | 58.10% | 49.20 | 30.80 | | |
| Donor 5.1 | Bead | 12.9 | 1.00E+08 | 28.90% | 1.67E+10 | 88.8% | 98.8% | 34.5% | 63.2% | 578.18 | 33.70 | 539.38 | 34.10 |
| Donor 5.2 | Bead | 12.9 | 1.00E+08 | 28.90% | 1.45E+10 | 85.3% | 98.5% | 30.0% | 67.5% | 500.58 | 34.50 | | |

It will be apparent to those skilled in the art that various modifications and variations can be made to the methods and structure of the present invention without departing from its scope. Thus it should be understood that the present invention is not be limited to the specific examples given. Rather, the present invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A method of expanding cells, the method comprising:
    introducing a first plurality of cells comprising leukocytes and red blood cells into a hollow fiber bioreactor, wherein the hollow fiber bioreactor comprises a plurality of hollow fibers and the first plurality of cells are generated using a leukapheresis procedure, wherein the first plurality of cells is added to the hollow fiber bioreactor without additional purification;
    exposing the first plurality of cells to an activator to activate expansion of the cells in the hollow fiber bioreactor;
    expanding at least a portion of the first plurality of cells comprising T cells in the plurality of hollow fibers of the bioreactor to generate a second plurality of expanded cells; and
    removing the second plurality of expanded cells from the bioreactor.

2. The method of claim 1, wherein the first plurality of cells comprise platelets.

3. The method of claim 2, wherein the first plurality of cells comprise granulocytes.

4. The method of claim 3, wherein the exposing comprises exposing the first plurality of cells to beads that comprise the activator on their surface.

5. The method of claim 4, wherein the activator comprises one or more antibodies selected from the group consisting of anti-CD2, anti-CD3, anti-CD28, and combinations thereof.

6. The method of claim 5, wherein the expanding comprises circulating media in the hollow fiber bioreactor.

7. The method of claim 6, wherein the media comprises one or more of, interleukin 2 (IL-2), interleukin 4 (IL-4), interleukin 5 (IL-5), interleukin 7 (IL-7), interleukin 15 (IL-15), and combinations thereof.

8. The method of claim 3, wherein the exposing comprises exposing the first plurality of cells to dendritic cells that comprise the activator.

9. The method of claim 8, wherein the activator comprises one or more antigens.

10. The method of claim 1, wherein the steps are performed in a closed system.

* * * * *